(12) United States Patent
Mullen et al.

(10) Patent No.: US 9,758,826 B2
(45) Date of Patent: Sep. 12, 2017

(54) PUMA, A PRO-APOPTOTIC GENE, AS A NOVEL MOLECULAR BIOMARKER FOR TNFα-INDUCED HUMAN ISLET DAMAGE

(75) Inventors: Yoko Mullen, Sherman Oaks, CA (US); Masato Mitsuhashi, Irvine, CA (US); Keiko Omori, Pasadena, CA (US)

(73) Assignees: City of Hope, Duarte, CA (US); Hitachi Chemical Research Center, Inc., Irvine, CA (US); Hitachi Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/163,326

(22) Filed: Jun. 17, 2011

(65) Prior Publication Data
US 2011/0318751 A1    Dec. 29, 2011

Related U.S. Application Data

(60) Provisional application No. 61/358,376, filed on Jun. 24, 2010.

(51) Int. Cl.
*C12Q 1/68* (2006.01)
*G01N 33/50* (2006.01)

(52) U.S. Cl.
CPC ......... *C12Q 1/6883* (2013.01); *G01N 33/507* (2013.01); *C12Q 2600/136* (2013.01); *C12Q 2600/158* (2013.01); *G01N 2333/4748* (2013.01); *G01N 2333/525* (2013.01)

(58) Field of Classification Search
CPC ............ C12Q 1/6883; C12Q 2600/136; C12Q 2600/158; G01N 2333/4748; G01N 2333/525; G01N 33/507
USPC ............................................... 435/6.12, 91.2
See application file for complete search history.

(56) References Cited

FOREIGN PATENT DOCUMENTS

WO    WO 2010015032 A1 *   2/2010

OTHER PUBLICATIONS

Gurzov et al. p53 Up-regulated Modulator of Apoptosis (PUMA) Activation Contributes to Pancreatic-Cell Apoptosis Induced by Proinflammatory Cytokines and Endoplasmic Reticulum Stress. J Biological Chem 2010;285(6):19910-20, Supplemental Data.*
McKenzie et al. Glucose Induces Pancreatic Islet Cell Apoptosis That Requires the BH3-Only Proteins Bim and Puma and Multi-BH Domain Protein Bax. Diabetes 2010;59:644-52.*
Iglesias et al. Comprehensive analysis of human pancreatic islets using flow and laser scanning cytometry. Transplantation Proceedings 2008;40:351-4.*
Omori et al. Improvement of human islet cryopreservation by a p38 MAPK inhibitor. American J Transplantation 2007;7:1224-32.*
Davalli et al., Cell Transplantation, vol. 17, pp. 1323-1336, 2008.*
Aggarwal, B. B., "Signalling Pathways of the TNF Superfamily: A Double-Edged Sword," Nat. Rev. Immunol. 3:745-756 (2003).
Bouzakri, K., et al., "MAP4K4 Gene Silencing in Human Skeletal Muscle Prevents Tumor Necrosis Factor-α-Induced Insulin Resistance," J. Biol. Chem. 282(11):7783-7789 (2007).
Danial, N. N., et al., "Cell Death: Critical Control Points," Cell 116:205-219.
De Vos, K., et al., "The 55-kDa Tumor Necrosis Factor Receptor Induces Clustering of Mitochondria Through Its Membrane-Proximal Region," J. Biol. Chem. 273(16):9673-9680 (1998).
Desagher, S., et al., "Mitochondria as the Central Control Point of Apoptosis," Trends Cell. Biol. 10:369-377 (2000).
Eizirik, D. L., et al., "The Role of Inflammation in Insulitis and β-Cell Loss in Type 1 Diabetes," Nat. Rev. Endocrinol. 5:219-226 (2009).
Eizirik, D. L., et al., "A Choice of Death—The Signal-Transduction of Immune-Mediated Beta-Cell Apoptosis," Diabetologia 44:2115-2133 (2001).
Grunnet, L. G., et al., "Proinflammatory Cytokines Activate the Intrinsic Apoptotic Pathway in β-Cells," Diabetes 58:1807-1815 (2009).
Gurzov, E. N., et al., "p53 Up-Regulated Modulator of Apoptosis (PUMA) Activation Contributes to Pancreatic β-Cell Apoptosis Induced by Proinflammatory Cytokines and Endoplasmic Reticulum Stress," J. Biol. Chem. 285(26):19910-19920 (2010).
Hagerkvist, R., et al., "Amelioration of Diabetes by Imatinib Mesylate (Gleevec®): Role of β-Cell NF-κB Activation and Anti-Apoptotic Preconditioning," FASEB J. 21:618-628 (2007).
Hanley, S., et al., "Tumor Necrosis Factor-α Production by Human Islets Leads to Postisolation Cell Death," Transplantation 82:813-818 (2006).
Held, W., et al., "Genes Encoding Tumor Necrosis Factor α and Granzyme A are Expressed During Development of Autoimmune Diabetes," Proc. Natl. Acad. Sci. USA 87:2239-2243 (1990).
Hengartner, M. O., "The Biochemistry of Apoptosis," Nature 407:770-776 (2000).
Hotamisligil, G. S., et al., "Tumor Necrosis Factor Alpha Inhibits Signaling from the Insulin Receptor," Proc. Natl. Acad. Sci. USA 91:4854-4858 (1994).
Hughes, K. J., et al., "Nitric Oxides Mediates a Shift from Early Necrosis to Late Apoptosis in Cytokine-Treated β-Cells that is Associated with Irreversible DNA Damage," Am. J. Physiol. Endocrinol. Metab. 297(5):E1187-1196 (2009).
Itakura, S., et al., "Mesenchymal Stem Cells Facilitate the Induction of Mixed Hematopoietic Chimerism and Islet Allograft Tolerance without GVHD in the Rat," Am. J. Transplant. 7:336-346 (2007).
Ito, T., et al., "Improvement of Canine Islet Yield by Donor Pancreas Infusion with a p38MAPK Inhibitor," Transplantation 86:321-329 (2008).

(Continued)

*Primary Examiner* — Cynthia B Wilder
(74) *Attorney, Agent, or Firm* — Perkins Coie LLP; Courtney Prochnow

(57) ABSTRACT p53-upregulated modulator of apoptosis (PUMA) is a biomarker associated with islet cell health. If PUMA is low, islet cells are typically healthy. If PUMA is high, islet cells are typically unhealthy or dying. PUMA may be measured by either measuring its nucleic or amino acid. PUMA mRNA may be induced by TNF-α stimulation in a time- and dose-dependent manner and β cell apoptosis is induced through a mitochondrial pathway. TNF-α significantly inhibited glucose-induced preproinsulin precursor mRNA synthesis. Such β cell stress signaling in human islets indicates overall state of islet health and, ultimately, the risk of onset and/or degree of severity of both type 1 and type 2 diabetes mellitus.

6 Claims, 35 Drawing Sheets

(56) References Cited

OTHER PUBLICATIONS

Jacob, C. O., et al., "Prevention of Diabetes in Nonobese Diabetic Mice by Tumor Necrosis Factor (TNF): Similarities Between TNF-α and Interleukin 1," Proc. Natl. Acad. Sci. USA 87:968-972 (1990).
Karin, M., et al., "NF-κB at the Crossroads of Life and Death," Nat. Immunol. 3(3):221-227 (2002).
Kim, H.E., et al., "Tumour Necrosis Factor-α-Induced Glucose-Stimulated Insulin Secretion Inhibition in INS-1 Cells is Ascribed to a Reduction of the Glucose-Stimulated $Ca^{2+}$ Influx," J. Endocrinol. 198:549-560 (2008).
Kwon, G., et al., "Tumor Necrosis Factor α-Induced Pancreatic β-cell Insulin Resistance is Mediated by Nitric Oxide and Prevented by 15-Deoxy-$\Delta^{12,14}$-Prostaglandin $J_2$ and Aminoguanidine," J. Biol. Chem. 274(26):18702-18708 (1999).
Louvet, C., et al., "Tyrosine Kinase Inhibitors Reverse Type 1 Diabetes in Nonobese Diabetic Mice," Proc. Nat. Acad. Sci. 105(48):18895-18900 (2008).
Lv, N., et al., "JANEX-1, a JAK3 Inhibitor, Protects Pancreatic Islets from Cytokine Toxicity Through Downregulation of NF-κB Activation and the JAK/STAT Pathway," Exp. Cell Res. 315-2064-2071 (2009).
Mastrandrea, L., et al., "Etanercept Treatment in Children with New-Onset Type 1 Diabetes," Diabetes Care 32:1244-1249 (2009).
McKenzie, M. D., et al., "Proapoptotic BH3-Only Protein Bid is Essential for Death Receptor-Induced Apoptosis of Pancreatic β-Cells," Diabetes 57:1284-1292 (2008).
Mitsuhashi, M., et al., "Ex Vivo Simulation of the Action of Antileukemia Drugs by Measuring Apoptosis-Related mRNA in Blood," Clin. Chem. 54(4):673-681 (2008).
Mitsuhashi, M., et al., "Ex Vivo Stimulation of IgG Fc and T-Cell Receptor Functions: An Application to Inflammatory Bowel Disease," Inflamm. Bowel Dis. 14:1061-1067 (2008).
Mitsuhashi, M., et al., "Ex Vivo Induction of mRNA in Human Whole Blood as a New Platform of Drug and Dietary Supplement Development," Pharm. Res. 25(5):1116-1124 (2008).
Mitsuhashi, M., et al., "Quantification of mRNA in Whole Blood by Assessing Recovery of RNA and Efficiency of cDNA Synthesis," Clin. Chem. 53(4):634-642 (2006).
Mitsuhashi, M., et al., "Quantification of Drug-Induced mRNA in Human Whole Blood Ex Vivo," Clin. Med. Blood Disorders 1:1-11 (2008).
Mitsuhashi, M., et al., "Gene Manipulation on Plastic Plates," Nature 357:519-520 (1992).
Morrison, T. B., et al., "Quantification of Low-Copy Transcripts by Continuous SYBR® Green I Monitoring During Amplification," BioTechniques 24:954-962 (1998).
Mueller, C., et al., "Accelerated β-Cell Destruction in Adoptively Transferred Autoimmune Diabetes Correlates with an Increased Expression of the Genes Coding for TNF-α and Granzyme A in the Intra-Islet Infiltrates," Diabetes 44:112-117 (1995).
Nakano, K., et al., "PUMA, A Novel Proapoptotic Gene, Is Induced by p53," Mol. Cell 7:683-694 (2001).
Niizuma, K., et al., "Potential Role of PUMA in Delayed Death of Hippocampal CA1 Neurons After Transient Global Cerebral Ischemia," Stroke 40:618-625 (2009).
Omori, K., et al., "Improvement of Human Islet Cryopreservation by a p38 MAPK Inhibitor," Am. J. Transplant. 7:1224-1232 (2007).
Omori, K., et al., "Microassay for Glucose-Induced Preproinsulin mRNA Expression to Assess Islet Functional Potency for Islet Transplantation," Transplantation 89(2):146-154 (2010).
Omori, K., et al., "P38 Alpha-Selective Mitogen Activated Protein Kinase Inhibitor for Improvement of Cultured Human Islet Recovery," Pancreas. 39(4):436-443 (2010).
Ortis, F., et al., "Induction of Nuclear Factor-κB and Its Downstream Genes by TNF-α IL-1β has a Pro-Apoptotic Role in Pancreatic Beta Cells," Diabetologia 51:1213-1225 (2008).
Picarella, D. E., et al., "Transgenic Tumor Necrosis Factor (TNF)-α Production in Pancreatic Islets Leads to Insulitis, Not Diabetes," J. Immunol. 150:4136-4150 (1993).
Plomgaard, P., et al., "Tumor Necrosis Factorα Induces Skeletal Muscle Insulin Resistance in Healthy Human Subjects Via Inhibition of Akt Substrate 160 Phosphorylation," Diabetes 54:2939-2945 (2005).
Reimertz, C., et al., "Gene Expression During ER Stress-Induced Apoptosis in Neurons: Induction of the BH3-Only Protein Bbc3/PUMA and Activation of the Mitochondrial Apoptosis Pathway," J. Cell Biol. 162(4):587-597 (2003).
Satoh, J., et al., "Recombinant Human Tumor Necrosis Factor α Suppresses Autoimmune Diabetes in Nonobese Diabetic Mice," J. Clin. Invest. 84:1345-1348 (1989).
Steinberg, G. R., et al., "Tumor Necrosis Factor-α-Induced Skeletal Muscle Insulin Resistance Involves Suppression of AMP-Kinase Signaling," Cell Metab. 4:465-474 (2006).
Stephens, L. A., et al., "Tumor Necrosis Factor-α-Activated Cell Death Pathways in NIT-1 Insulinoma Cells and Primary Pancreatic β Cells," Endocrinol. 140(7): 3219-3227 (1999).
Suk, K., et al., "IFN-γ/TNF-α Synergism as the Final Effector in Autoimmune Diabetes: A Key Role for STAT1/IFN Regulatory Factor-1 Pathway in Pancreatic β Cell Death," J. Immunol. 166:4481-4489 (2001).
Sun, Q., et al., "PUMA Mediates EGFR Tyrosine Kinase Inhibitor-Induced Apoptosis in Head and Neck Cancer Cells," Oncogene 28(24):2348-2357 (2009).
Tesz, G. J., et al., "Tumor Necrosis Factor α (TNFα) Stimulates Map4k4 Expression Through TNFα Receptor 1 Signaling to c-Jun and Activating Transcription Factor 2," J. Biol. Chem. 282(27):19302-19312 (2007).
Thomas, H. E., et al., "Evidence That β Cell Death in the Nonobese Diabetic Mouse is Fas Independent," J. Immunol. 163:1562-1569 (1999).
Todorov, I., et al., "Quantitative Assessment of β-Cell Apoptosis and Cell Composition of Isolated, Undisrupted Human Islets by Laser Scanning Cytometry," Transplantation 90:836-842 (2010).
Toth, A., et al., "Targeted Deletion of Puma Attenuates Cardiomyocyte Death and Improves Cardiac Function During Ischemia-Reperfusion," Am. J. Physiol. Heart Circ. Physiol. 291:H52-H60 (2006).
Uysal, K. T., et al., "Protection from Obesity-Induced Insulin Resistance in Mice Lacking TNF-α Function," Nature 389:610-614 (1997).
Vousden, K. H., "p53 and PUMA: A Deadly Duo," Science 309:1685-1686 (2005).
Wajant, H., et al., "Tumor Necrosis Factor Signal," Cell Death and Differentiation 10:45-65 (2003).
Wang, P., et al., "PUMA is Directly Activated by NF-κB and Contributes to TNF-α-Induced Apoptosis," Cell Death Differ. 16(9):1192-1202 (2009).
Wu, B., et al., "p53 Independent Induction of PUMA Mediates Intestinal Apoptosis in Response to Ischaemia-Reperfusion," Gut 56:645-654 (2007).
Yang, X.D., et al., "Effect of Tumor Necrosis Factor α on Insulin-Dependent Diabetes Mellitus in NOD Mice. I. The Early Development of Autoimmunity and the Diabetogenic Process," J. Exp. Med. 180:995-1004 (1994).
You, H., et al., "FOX03a-Dependent Regulation of Puma in Response to Cytokine/Growth Factor Withdrawal," JEM 203(7):1657-1663 (2006).
Yu, J., et al., "PUMA Mediates the Apoptotic Response to p53 in Colorectal Cancer Cells," Proc. Nat. Acad. Sci. 100(4):1931-1936 (2003).

* cited by examiner

| | TNFα | | | | | |
|---|---|---|---|---|---|---|
| | 200 (ng/mL) | | 20 (ng/mL) | | 2 (ng/mL) | |
| mRNA | fold increase | P | fold increase | P | fold increase | P |
| β actin | 1.17±0.09 | n.s. | 1.06±0.62 | n.s. | 0.92±0.65 | n.s. |
| TNFα | 2.24±0.45 | 0.01 | 2.9±0.17 | <0.01 | 1.14±0.03 | n.s. |
| IL-1β | 2.9±0.99 | 0.03 | 2.24±0.06 | 0.02 | 1.15±0.46 | n.s. |
| IFN-γ | 6.38±2.23 | 0.01 | 5.46±0.85 | <0.01 | 0.83±0.39 | n.s. |
| IL-6 | 5.55±1.22 | 0.01 | 5.76±1.13 | 0.01 | 2.05±1.31 | n.s. |
| IL-8 | 4.32±1.16 | 0.01 | 4.54±0.19 | 0.03 | 1.25±0.29 | n.s. |
| PUMA | 1.24±0.13 | n.s. | 1.13±0.11 | n.s. | 0.23±0.10 | n.s. |
| P21 | 1.45±0.44 | n.s. | 1.67±0.16 | n.s. | 1.47±0.23 | n.s. |

Fig. 10 (cont.)
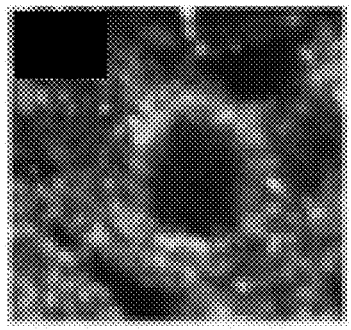
Fig. 10G
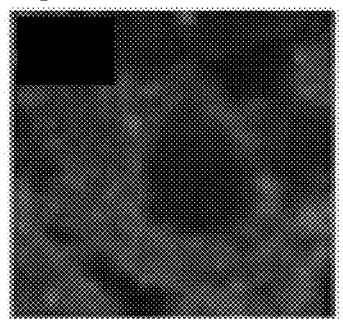
Fig. 10H
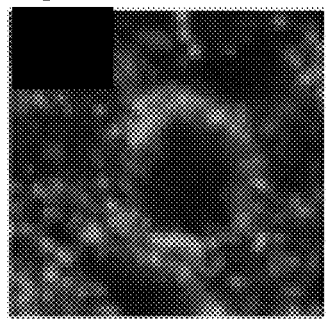
Fig. 10I
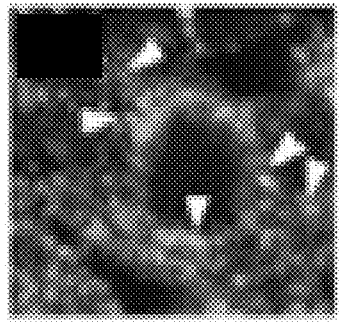
Fig. 10J
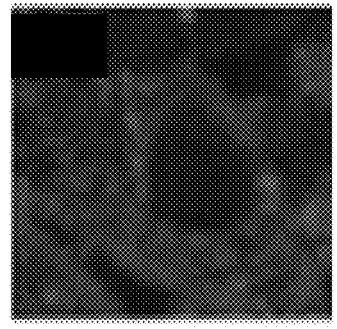
Fig. 10K
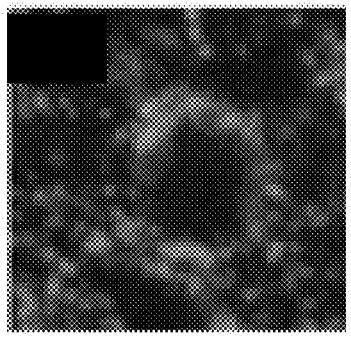
Fig. 10L Fig. 10M Merged  Fig. 10N PUMA  Fig. 10O Insulin Fig. 10P Merged  Fig. 10Q PUMA  Fig. 10R Glucagon

A

B

A

B

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: In1 upstream probe
```

<400> SEQUENCE: 1
aggtgggctc aggattcca                                                    19

<210> SEQ ID NO 2
<211> LENGTH: 19
<212> TYPE: DNA
<213> ORGANISM: Artificial Sequence
<220> FEATURE:
<223> OTHER INFORMATION: In1 downstream probe

<400> SEQUENCE: 2 tcaccccac atgcttcac                                                     19

<210> SEQ ID NO 3
<211> LENGTH: 20
<212> TYPE: DNA
<213> ORGANISM: Artificial Sequence
<220> FEATURE:
<223> OTHER INFORMATION: In2 upstream probe

<400> SEQUENCE: 3
actcgcccct caaacaaatg                                                   20

<210> SEQ ID NO 4
<211> LENGTH: 21
<212> TYPE: DNA
<213> ORGANISM: Artificial Sequence
<220> FEATURE:
<223> OTHER INFORMATION: In2 downstream probe

<400> SEQUENCE: 4
tgaatctgcg gtcatcaaat g                                                 21

<210> SEQ ID NO 5
<211> LENGTH: 19
<212> TYPE: DNA
<213> ORGANISM: Artificial Sequence
<220> FEATURE:
<223> OTHER INFORMATION: In2Ex3 upstream probe

<400> SEQUENCE: 5
ctctgcctcg ccgctgttc                                                    19

<210> SEQ ID NO 6
<211> LENGTH: 20
<212> TYPE: DNA
<213> ORGANISM: Artificial Sequence
<220> FEATURE:
<223> OTHER INFORMATION: In2Ex3 downstream probe

<400> SEQUENCE: 6
tccacaatgc cacgcttctg                                                   20

<210> SEQ ID NO 7
<211> LENGTH: 20
<212> TYPE: DNA
<213> ORGANISM: Artificial Sequence
<220> FEATURE:
<223> OTHER INFORMATION: Ex2a upstream probe

<400> SEQUENCE: 7
gcagcctttg tgaaccaaca                                                   20

<210> SEQ ID NO 8

```
<211> LENGTH: 22
<212> TYPE: DNA
<213> ORGANISM: Artificial Sequence
<220> FEATURE:
<223> OTHER INFORMATION: Ex2a downstream probe

<400> SEQUENCE: 8
ttccccgcac actaggtaga ga                                              22

<210> SEQ ID NO 9
<211> LENGTH: 22
<212> TYPE: DNA
<213> ORGANISM: Artificial Sequence
<220> FEATURE:
<223> OTHER INFORMATION: Ex2b upstream probe

<400> SEQUENCE: 9
gggaacgagg cttcttctac ac                                              22

<210> SEQ ID NO 10
<211> LENGTH: 19
<212> TYPE: DNA
<213> ORGANISM: Artificial Sequence
<220> FEATURE:
<223> OTHER INFORMATION: Ex2b downstream probe

<400> SEQUENCE: 10
ccacaatgcc acgcttctg                                                  19

<210> SEQ ID NO 11
<211> LENGTH: 23
<212> TYPE: DNA
<213> ORGANISM: Artificial Sequence
<220> FEATURE:
<223> OTHER INFORMATION: Ex3 upstream probe

<400> SEQUENCE: 11
cattgtggaa caatgctgta cca                                             23

<210> SEQ ID NO 12
<211> LENGTH: 18
<212> TYPE: DNA
<213> ORGANISM: Artificial Sequence
<220> FEATURE:
<223> OTHER INFORMATION: Ex3 downstream probe

<400> SEQUENCE: 12
gcctgcgggc tgcgtcta                                                   18
```

PUMA, A PRO-APOPTOTIC GENE, AS A NOVEL MOLECULAR BIOMARKER FOR TNFα-INDUCED HUMAN ISLET DAMAGE

PRIORITY CLAIM

This application claims priority to U.S. Provisional Application No. 61/358,376, filed Jun. 24, 2010, which is incorporated herein by reference.

GOVERNMENT INTEREST

The present invention was made with government support under National Institutes of Health grant number U42RR16607. The government may have certain rights in the present invention.

BACKGROUND

Beta cells ("β cells") are a type of islet cell found in the pancreas that produce and secrete the hormone insulin. Insulin controls levels of glucose in blood. Type 1 diabetes mellitus (T1DM) is an autoimmune disease characterized by the selective destruction of pancreatic β cells, while type 2 diabetes mellitus (T2DM) is a metabolic disorder characterized by insulin resistance and a loss of β cell function and mass. β cell apoptosis is central to disease progression in both T1DM and T2DM. Preventing β cell apoptosis is a key factor in the successful outcome of islet transplantation as a treatment for T1DM. Proinflammatory cytokines, such as tumor necrosis factor-α (TNF-α), interleukin-β (IL-1β), interferon-γ (IFN-γ), oxygen free radicals, and nitric oxide are implicated in promoting β cell death (1, 2). Although the role of TNF-α as an effector remains ambiguous (3-8), a combination of IFN-γ and TNF-α synergistically induces β cell apoptosis, and is a key factor in the development of autoimmune diabetes (9). In T2DM, TNF-α is a key mediator in insulin resistance associated with obesity (10-12). TNF-α not only induces insulin resistance in insulin-sensitive tissues, such as adipose tissue and skeletal muscle (13-15), but also decreases glucose stimulated insulin secretion (GSIS) in β cells (14). These findings suggest that TNF-α mediates dysfunction and/or destruction of β cells in both T1DM and T2DM.

Inflammation contributes to β cell destruction, prolonged suppression of β cell function, inhibition of β cell regeneration, and even peripheral insulin resistance (34). Cytokine induced cell death has been shown to contribute to β cell apoptosis through an intrinsic pathway (21, 22). The proinflammatory cytokine TNF-α has been shown to play an important role in the pathogenesis of T1DM as well as T2DM. Human islets express a high level of tumor necrosis factor receptor superfamily (TNFRSF) 1A. Since mRNAs of ligands for TNFRSF1A are constitutively expressed in peripheral blood leukocytes and are induced at a high levels by stimulation (35, 36), receptors for TNF-α on islet cells would play a significant role in inflammation.

TNF-α can induce both apoptotic and anti-apoptotic signals regulated by the activation of NFκB (16-18). TNF-α mediated apoptosis through the TNF receptor associated death domain (TRADD), where specific ligand-receptor binding leads first to activation of Caspase-8 and then to activation of Caspase-3 via an extrinsic pathway (19). Alternatively, apoptosis through intracellular or intrinsic pathways is caused by DNA damage, hypoxia, nutrient deprivation, or reactive oxygen species (ROS) function via the mitochondrial pathway and tightly modulated by the Bcl-2 proteins (also called mitochondrial pathway or Bcl-2 regulated pathway). These triggering factors lead to mitochondrial membrane permeability and a subsequent release of cytochrome c from the intermembranous space, followed by the activation of Caspase-9, which in turn activates Caspase-3 (20). Bcl-2 homology 3 (BH3) only protein, Bid (BH3 interacting domain death agonist), is shown to be essential for death receptor-induced apoptosis of pancreatic β cells in mice (21). IL-1-β, IFN-γ and/or TNF-α induce cell death in rat islets through the intrinsic pathway by dephosphorylation of the BH3 only protein, Bad (BCL2-associated agonist of cell death) (22). However, interactions between extrinsic and intrinsic pathways in cytokine induced cell death of human pancreatic β cells remains unclear.

PUMA (p53 upregulated modulator of apoptosis) is one of the most potent killers among the BH3-only subgroup of Bcl-2 member protein (23, 24). It is induced by p53 following DNA damage, irradiation or chemotherapeutic drugs (25). PUMA/BBC3 (Bcl-2 binding component 3) can be directly activated through p53 responsive elements in its promoter region (26) or independently of p53 by other transcription factors initiating apoptotic responses, including growth factor/cytokine deprivation (27), endoplasmic reticulum stress (28), and ischemia reperfusion (29, 30). PUMA is also activated by the p65 component of NF-κB through a κB site in the PUMA promoter in response to TNF-α (31). It would be a significant improvement in the art to understand and measure the role of PUMA in islet cell death, particularly in β cell specific death, which has heretofore been unknown. It would also be a significant improvement to use such understanding to develop PUMA as a biomarker and to make and use PUMA-based therapies for controlling islet cell apoptosis.

SUMMARY

The present methods, assays, and screens measure PUMA (p53-upregulated modulator of apoptosis) as a molecular biomarker to assess tumor necrosis factor-α (TNF-α) induced β cell stress signaling in human islets, to indicate the health of the islet cell expressing PUMA, and to search for and administer drugs that reduce PUMA expression and/or effect, thus increasing islet cell health. "Islet cell health" or "islet health" or "health of an islet cell" or similar phrase, as used herein, is intended to mean the present physiological condition of the cell, including, but not limited to, the cell's current and continued viability, wellness and/or continued normal functioning of an islet cell. If the islet cell is a beta cell, "islet health" also indicates the cell's ability to produce insulin normally. Decreased metabolism, apoptosis, or other cellular decline or death is a reduction or elimination of islet cell health.

Preferably, PUMA is measured by the amount of PUMA nucleic acid, such as mRNA or cDNA, that is present in or around the islet cell. PUMA amino acid may also be measured. In one embodiment, an assay determines biosynthetic capacity of islets by measuring glucose-induced preproinsulin precursor mRNA or mRNA synthesis from a set of single human islets. This assay allows precursor mRNA or mRNA expression of islets to be examined in multiple conditions using a small number of islets, which is a major advantage for in vitro islet testing. Such β cell stress signaling in human islets also indicates overall state of islet health and, ultimately, the risk of onset and/or degree of severity of both type 1 and type 2 diabetes mellitus and/or obesity and its related conditions, such a high blood pressure and increased risk of stroke.

The present experiments have revealed that PUMA mRNA is induced by TNF-α stimulation in a time- and dose-dependent manner and β cell apoptosis is induced through a mitochondrial pathway. Furthermore, TNF-α significantly inhibited glucose-induced preproinsulin precursor mRNA synthesis, which inversely correlates with PUMA mRNA expression measured in the corresponding islets. β cell stress signaling in human islets can be utilized to screen the quality of islets and screen drugs candidates and compounds that protect islets from TNF-α induced toxicity.

A screen for a compound that protects or improves islet cell health is contemplated. Such a screen would require taking a measurement of or previously knowing the level of PUMA expression in the islet cell being tested, and then administering one or more test compounds to the islet cell. Preferably, the islet cell or group of cells is isolated in vitro for the screen. Then, after the compound or combination of compounds has been given sufficient time to affect the PUMA level in the cell, post-administration measurement of the PUMA level is taken. If the PUMA level has decreased, then the compound or combination of compounds protects or improves islet health by antagonizing PUMA production in the cell. Multiple measurements can be taken over time and one or multiple compounds can be tested in combination and administered simultaneously or at staggered time points. If the level of PUMA is unchanged after administration of the test compound, the compound likely has no effect on the level of PUMA in an islet cell. If the PUMA level increases after administration of the test compound, then it has a negative effect on islet health and should be discarded as a candidate. If multiple compounds are administered, then the test should be designed in a way to determine both individual and combined effects of the compounds. The effect of compounds may be assayed by testing levels of PUMA in the islet cells with TNF-α stimulation. Islets are pre-incubated with a compound and then stimulated with TNF-α. If the PUMA level does not increase by TNF-α stimulation, it indicates that the compound has a protective effect on islets from TNF-α mediated damage. The level of PUMA may be measured by measuring nucleic acid or amino acid or both. If nucleic acid is measured, it may be PUMA mRNA or PUMA cDNA. The effect of compounds to protect islets or improve islet health may be further confirmed by detecting and/or measuring the glucose-induced preproinsulin precursor mRNA along with PUMA mRNA in the islet cells. The compound or compounds found to protect or improve islet health may then be administered to patients for the treatment of diabetes.

The health of islet cells may be assayed by testing levels of PUMA in the islet cells before and/or after induction by TNF-α stimulation. Such testing may be used to determine the viability and/or quality of isolated islet cells, pancreatic tissues, or a whole pancreas to be transplanted.

In another embodiment, a patient at risk for type 1 and/or type 2 diabetes has an islet health test. The test comprises assaying islet cells for levels of PUMA mRNA in the islet cells after induction by TNF-α stimulation. The assay can be conducted in vitro using a pancreatic biopsy sample or conducted in vivo by cell assay or other collection of biological samples. The higher the level of PUMA mRNA in the islet cells, the greater the risk of developing type 1 and/or type 2 diabetes.

In yet another embodiment, a patient who has been diagnosed with type 1 and/or type 2 diabetes can have the progression of diabetes tested by assaying a pancreatic biopsy sample for levels of PUMA mRNA in the islet cells after induction by TNF-α stimulation. The level of PUMA expression is tested once or, preferably, more than once at various time points relevant to determining the progression of diabetes. The higher the level of PUMA mRNA, the more severe or progressed the type 1 and/or type 2 diabetes is in the patient. The effectiveness of diabetes treatments may also be measured by taking a PUMA measurement before beginning the diabetes treatment and then taking one or more PUMA measurements during treatment. If the level of PUMA is decreasing, it is an indication that the treatment is working. However, if the level of PUMA remains the same or is increasing, it is an indication that the treatment is ineffective.

Methods of silencing PUMA mRNA to prevent apoptosis of islet cells are also described and include both transcriptional and post-transcriptional gene silencing. In one instance, transcriptional gene silencing results from histone modifications such that the gene is not accessible to transcriptional machinery such as RNA polymerase and transcription factors. Post-transcriptional gene silencing may result when the PUMA mRNA is blocked or destroyed to prevent translation. RNAi may also be used to silence PUMA mRNA.

Anti-PUMA compounds may be administered alone or as part of a composition comprising the compound. The compound may be nucleic acid, amino acid, small molecule, or any other compound that reduces PUMA expression or PUMA's negative effect on islet cell health. The composition may target PUMA function directly by down-regulating PUMA expression, by inhibiting binding of PUMA to interacting proteins, including but not limited to Bcl-2 or Bcl-xL, or by inhibiting the mitochondrial translocation of Bax. The composition may further inhibit, alone or in combination with the above, some other PUMA function. The composition may be delivered in any effective manner and may be delivered and/or utilized alone or in combination with another therapy.

Kits, including instructions, reagents, and tubes, and plates, for carrying out the assays and methods of the present invention are also contemplated.

BRIEF DESCRIPTION OF THE DRAWINGS

FIG. 4. PUMA, IL-8 and TNF-α are used as markers to screen drug compounds protecting islets from TNF-α stimulus. Single human islets in hextuplicate were pre-incubated with various drugs (all used at 10 μM except Etanercept (0.1μ/ml)) or solvent (DMSO) at 37° C. for 1 hour, followed by stimulation with or without 5 ng/ml of TNF-α for an additional 4 hours.

FIG. 9. Since isolated islets are not totally free of blood, PUMA and IL-8 expressed in human islets by TNF-α stimulation may derive from cells circulating in blood. However, PUMA is not induced by TNF-α in human whole blood. TNF-α (2, 20, 200 ng/ml) was mixed with heparinized whole blood and incubated at 37° C. for 4 hours. Various mRNA were quantified using the method descried previously (44). >20 ng/ml TNF-α induced both IL-8 and endogenous TNF mRNA but at lower levels. PUMA mRNA was not induced by TNF-α even with the highest dose (200 ng/mL) used with islet experiments.

FIGS. 10A-10F. Arrows in FIGS. 10A, C, D and F indicate mitochondria clustered in perinuclear region. In FIGS. 10G-10L, a representative β-cell treated with TNF-α+IFN-γ and expressing PUMA, which is in the area highlighted in FIG. 10D, is enlarged. The individual staining is shown in FIGS. 10K (PUMA), and FIG. 10L (Cox IV). Merged double staining is shown in FIGS. 10H (PUMA and insulin), FIG. 10I (Cox IV and insulin), and FIGS. 10J (PUMA and Cox IV). FIG. 10G shows triple staining (PUMA, Cox IV and insulin). The arrows in FIG. 10J indicate the co-localization of PUMA and mitochondria. FIGS. 10M-R: Paraffin sections of pancreas tissue taken after cold preservation and before islet isolation not treated with TNF-α or IFN-γ were stained for PUMA (FIGS. 10N and 10Q) and insulin (FIG. 10O) or glucagon (FIG. 10R). Images are representative of three independent cases. Bar=20 μm (FIGS. 10A-F) or 50 μm (FIGS. 10M-R).

DETAILED DESCRIPTION

PUMA levels are inversely proportional to the health of an islet cell and pancreatic health in general. Suppressing or silencing PUMA reduces or stops islet cell apoptosis. The expression of PUMA in human islets is examined in response to TNF-α stimulation. Accordingly, measuring PUMA as a biomarker allows a determination of the state of islet health and controlling PUMA expression allows for management of islet health and insulin production.

In a present embodiment, using a newly developed method to assess gene expressions using a set of single human islets, a pro-apoptotic gene, PUMA/BBC3 (p53-upregulated modulator of apoptosis/Bcl-2 binding component 3), is up-regulated in human islets stimulated by recombinant TNF-α alone or in combination with interferon (IFN)-γ in time and dose dependent manner. The up-regulation of PUMA is associated with an activation of nuclear factor-κB (NF-κB) and induced β cell apoptosis through a mitochondrial pathway and is enhanced by IFN-γ. Up-regulation of PUMA by TNF-α is associated with increased cleaved caspase-9 and cleaved caspase-3, but undetectable with cleaved caspase-8, indicating that TNF-α induced PUMA expression leads to islet cell apoptosis through an intrinsic pathway.

PUMA up-regulation is also associated with the abrogation of glucose-stimulated preproinsulin mRNA synthesis in the islet. Silencing PUMA by transfecting small interfering PUMA RNA into a β cell line reduced cell death induced by TNF-α and IFN-γ. Furthermore, PUMA expression levels in islets negatively correlated with in vivo islet function following transplantation into STZ-diabetic NODscid mice. Results show that the increased PUMA expression levels negatively impact β cell function in vitro and in vivo, which can be used as an early biomarker to detect TNF-α induced β cell stress and may contribute to the discovery and characterization of islet-protecting compounds for the treatment of diabetes.

The present experiments further demonstrate that PUMA is a marker for TNF-α-induced cellular damages in human islets. In addition to the pathway involving Bid, a bcl-2 family gene important in death receptor-induced mouse β cell death, multiple pathways may be involved in the PUMA expression mediated by TNF-α and IFNγ. The inhibition of NFκB by islet pre-incubation with BAY 11-7082 did not inhibit PUMA expression. Since IFN-γ further augmented TNF-α induced PUMA and PUMA expression, the IFN-γ mediated cell death pathway. As explained herein, the JAK/STAT pathway may also be involved.

In addition to TNF-α, the expression of PUMA was examined following stimulation with IL-1β. IL-1β alone stimulation induced PUMA, IL-8, TNF and IL1B mRNA within 4 hours. However, unlike TNF-α-induced PUMA, IL-1β-induced PUMA expression returned to the normal level by 16 hours. IL-1β-induced PUMA expression can also be explained through the NFκB pathway. See FIGS. 16A-D.

Figure 2A:
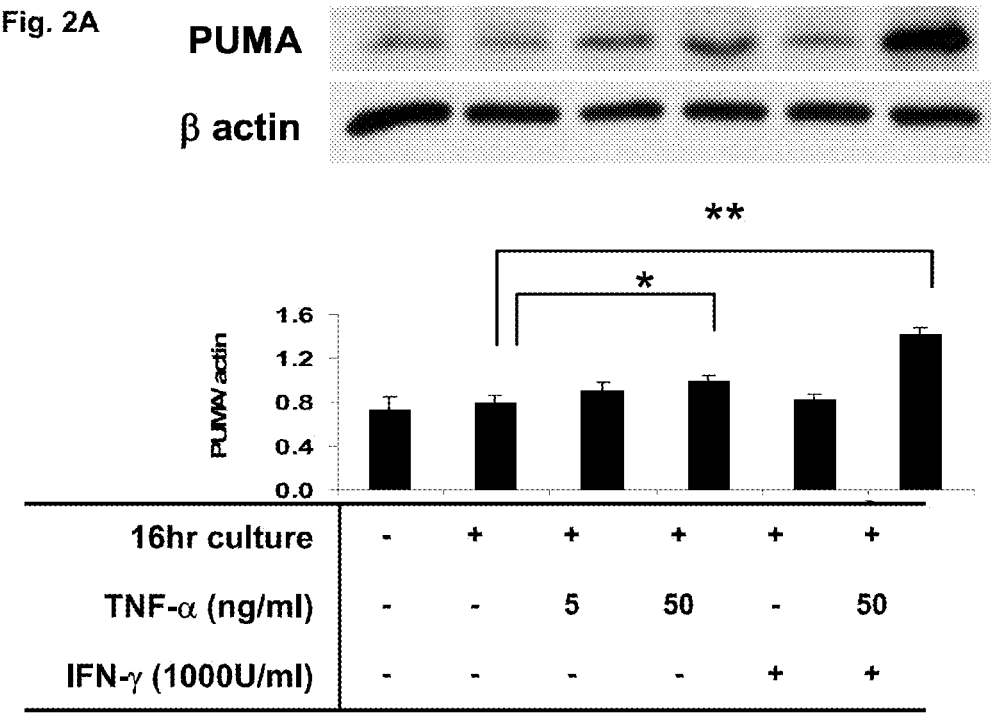
FIG. 2 demonstrates that IFNγ alone does not induce PUMA but enhances TNF-α-induced PUMA expression. A) 500 islet equivalents (IEQs) were cultured with or without TNF-α (5 and 50 ng/ml) and/or IFNγ (1000 U/ml) for 24 hours. Cell lysate was used for western blot to examine the PUMA expression in islets (*p<0.05, **p<0.005, n=3). B) Up regulation of PUMA was associated with increased phosphorylation of the p-p65 component (Ser536) of NFκB. (p=NS, n=3). C) Islets pre-incubated with NFκB inhibitor, BAY 11-7082, for 1 hour prior to TNF-α (50 ng/ml) or in combination with IFNγ (1000 U/ml) stimulation were examined by western blot to determine PUMA expression (n=3). D) Islets pre-incubated with NFκB inhibitor, BAY 11-7082, for 1 hour prior to TNF-α (50 ng/ml) stimulation were examined by western blot to determine PUMA expression (n=3). All data are presented as a mean±standard error. The bar graph shows target protein expression normalized by β actin. PUMA protein was translationally up-regulated in human islets by TNF-α, but not by IFNγ alone. The upregulation of PUMA by TNF-α was enhanced by the addition of IFNγ. Although PUMA expression in TNF-α stimulated islets increased in response to NFκB activation, the NFκB inhibitor BAY11-7082 did not inhibit PUMA expression induced by the combination of TNF-α and IFN-γ, indicating that another pathway than NFκB is involved.
Figure 3A:
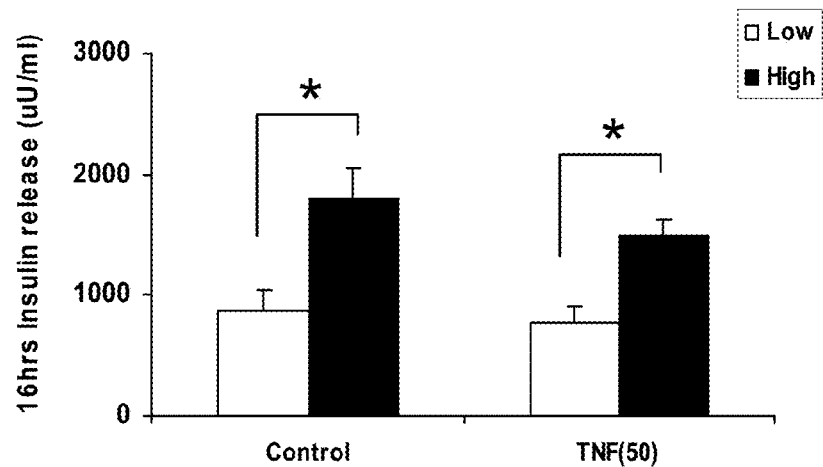
FIG. 3. TNF-α, but not IFNγ, impairs glucose induced preproinsulin precursor mRNA in human islets. A) Insulin content of medium supernatant from a single human islet culture in hextuplicate during 16 hours in low- or high-glucose media with or without 50 ng/ml TNF-α was measured. B) The glucose induced newly synthesized preproinsulin precursor mRNA measured by pre-spliced preproinsulin mRNA normalized by pre- and post-spliced preproinsulin mRNA (% exon) in the corresponding islets with or without 50 ng/ml. TNF-α was also examined (n=3, *p<0.05). C) Glucose induced preproinsululin precursor mRNA synthesis with or without TNF-α (1, 5 and 50 ng/ml) and/or IFNγ (10, 100 and 1000 U/ml) from a single human islet in hextuplicate. D) Correlation between PUMA mRNA and INS precursor mRNA levels in islets cultured in high-glucose media treated with TNF-α (1, 5 and 50 ng/ml), IFN-γ (10, 100 and 1000 U/ml) or a combination of both for 16 hours. The data points are from a total of 53 single islets (r=−0.45, p<0.001). All data are presented as a mean±standard error. TNF-α did not change insulin release but preproinsulin precursor mRNA synthesis was completely abolished over 16 hours in human islets.
Figure 3B:
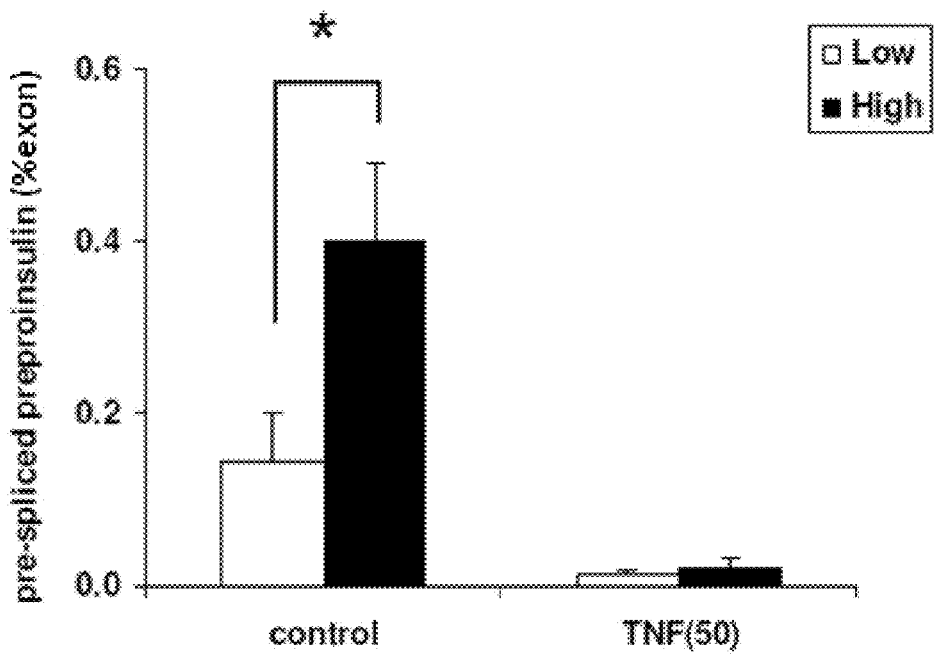
Figure 3C:
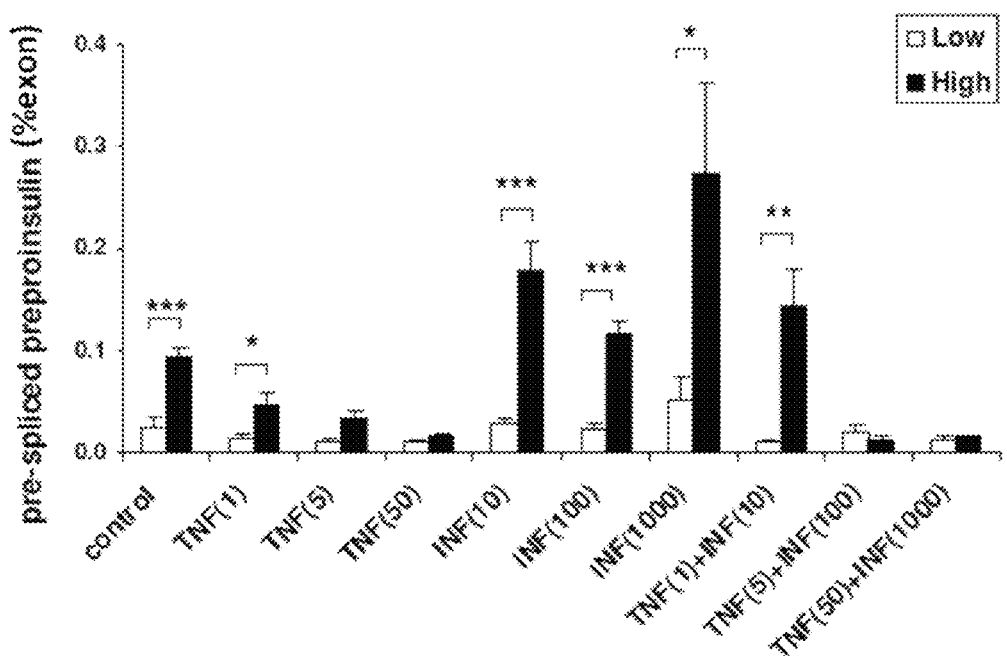
Figure 4A:
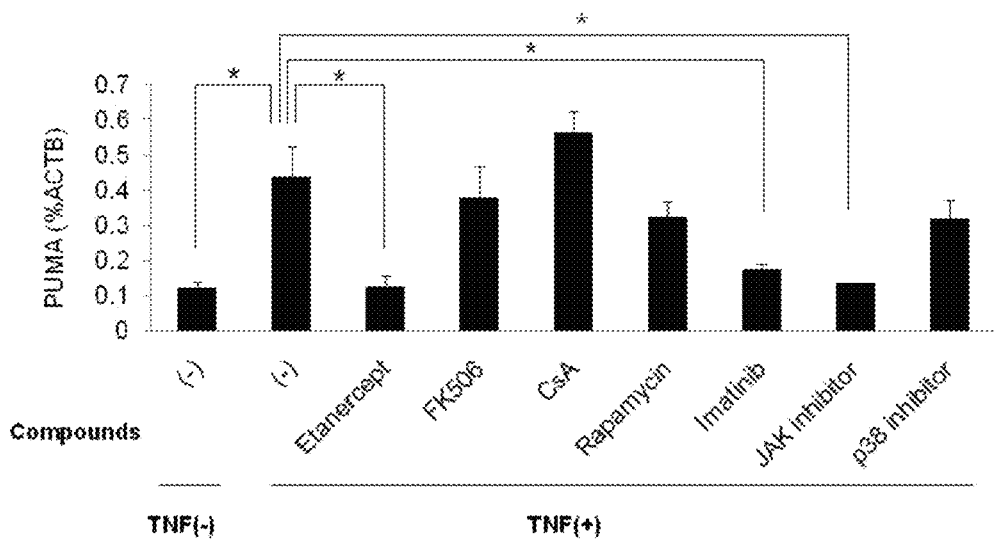
FIG. 4A: PUMA and ACTB mRNA were quantified and the results are expressed as % ACTB (*p<0.05 vs. control islets with TNF-α).
Figure 4B:
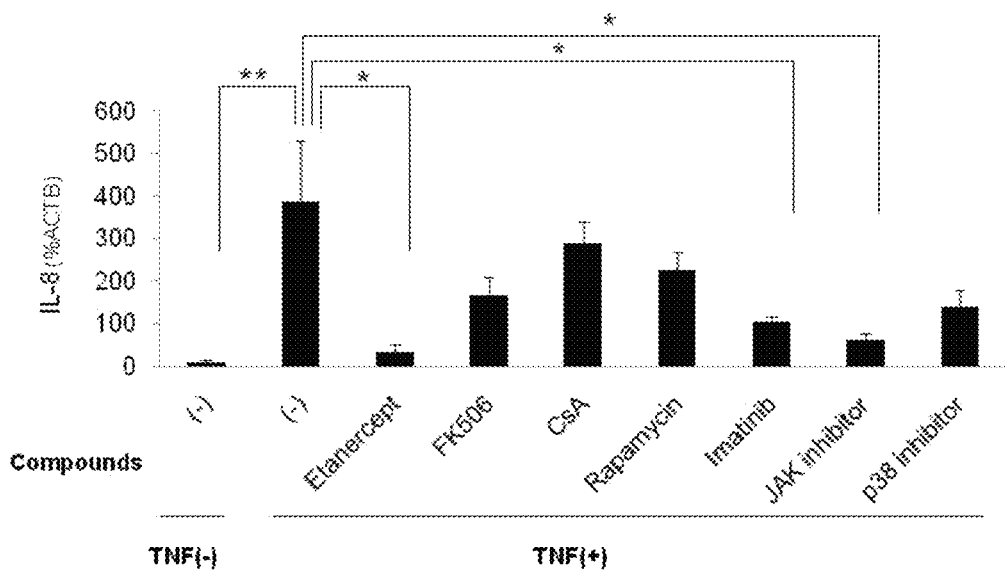
FIG. 4B: IL-8 was quantified and the results are expressed as % ACTB.
Figure 4C:
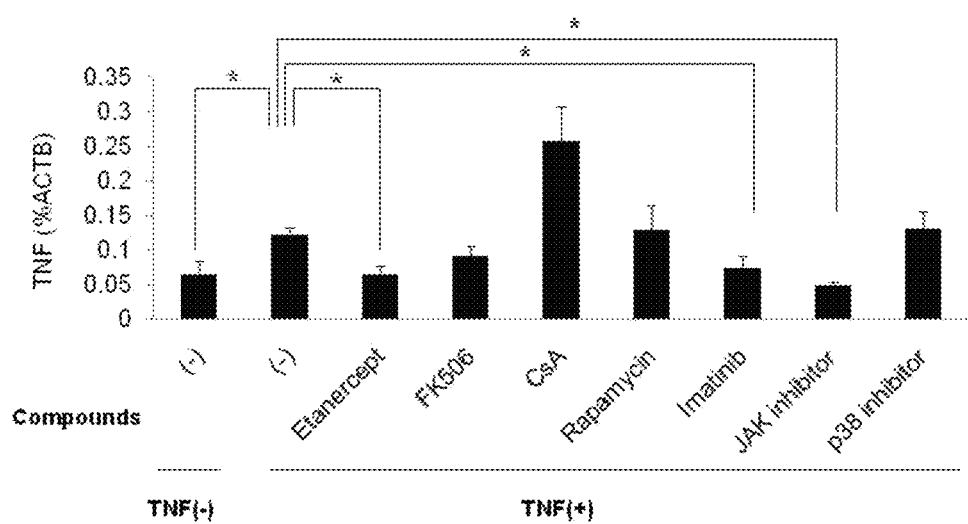
FIG. 4C; Endogenous TNF-α was quantified and the results are expressed as % ACTB. Together, the results of FIG. 4 show an example of a compound screening system using PUMA, IL-8 and TNF mRNA. TNF-α receptor blocker, Etanercept, successfully inhibited the up-regulation of PUMA, IL-8 and TNF mRNA induced by the assay control (TNF-α stimulus alone). This screening system also showed that tyrosine inhibitor, Imatininb, and a JAK inhibitor protects islets from TNF-α induced apoptosis.
Figure 5A:
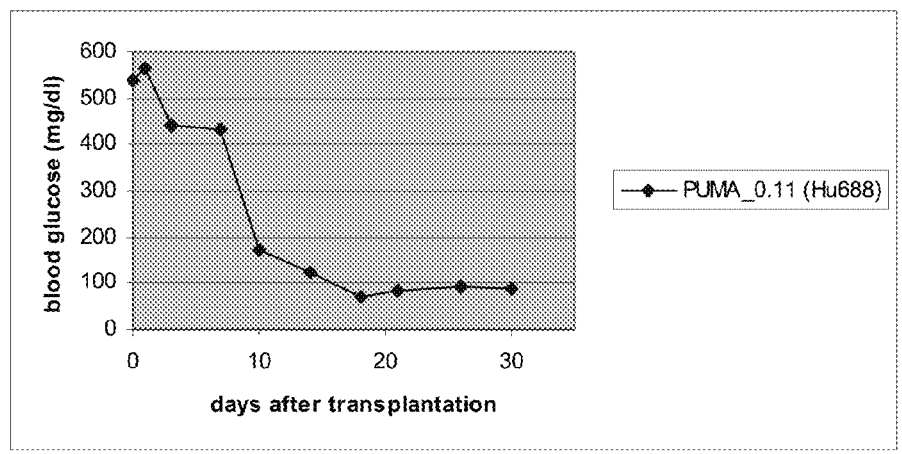
FIG. 5. Each of FIGS. 5A-5J, changes in blood glucose levels in individual lot islets is shown. 1200 IEQ were transplanted under the renal capsule of each NODscid mouse made diabetic with STZ. Each line represents a mouse. It takes two to four weeks for transplanted islets to fully function and islets with marginal quality show the fractured blood glucose level during this period.
Figure 5B:
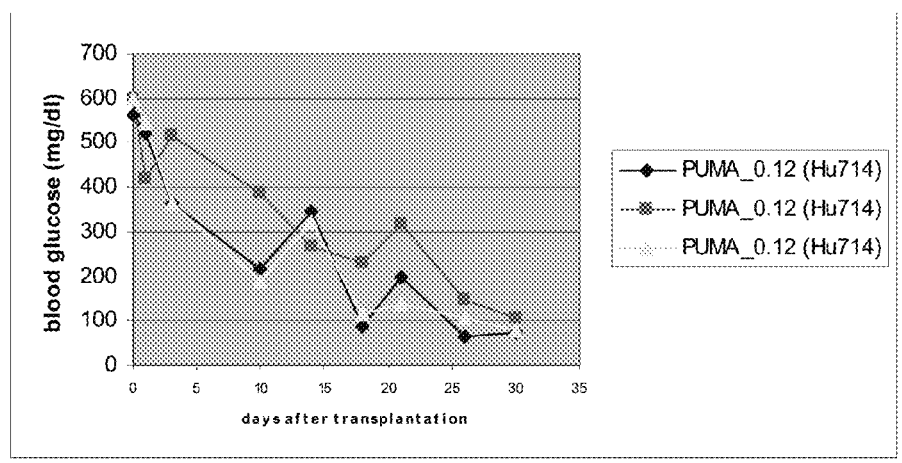
Figure 5C:
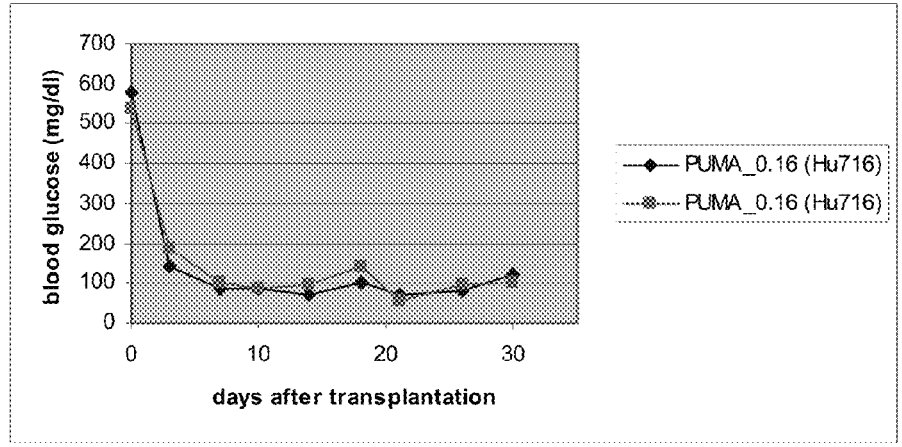
Figure 5D:
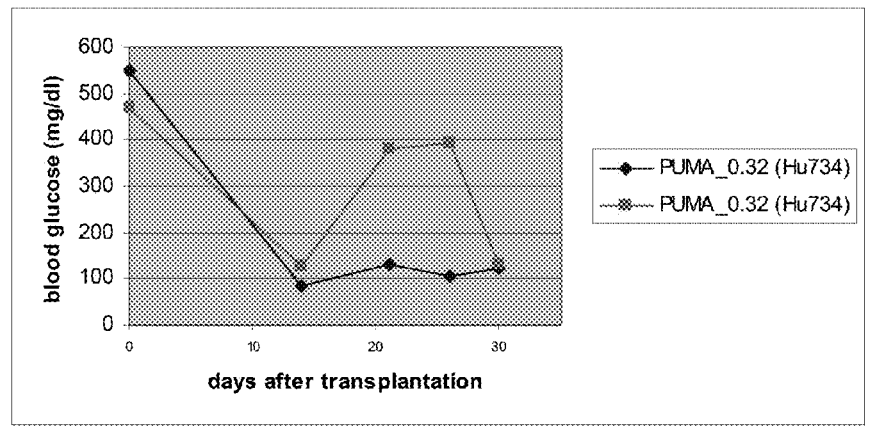
Figure 5E:
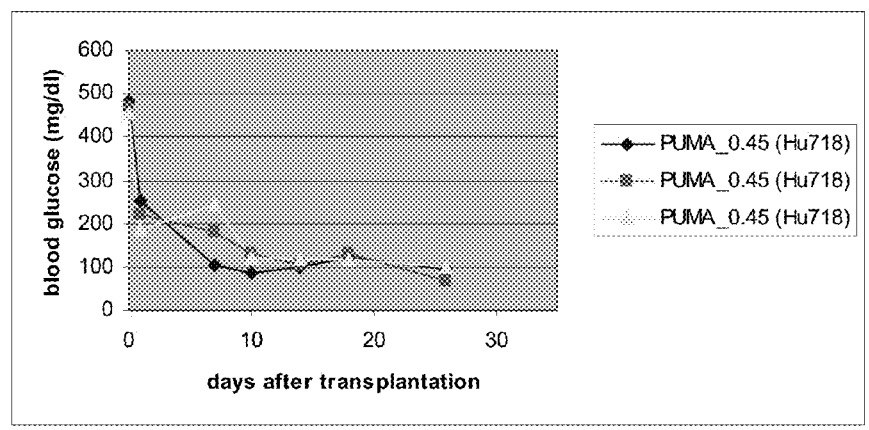
Figure 5F:
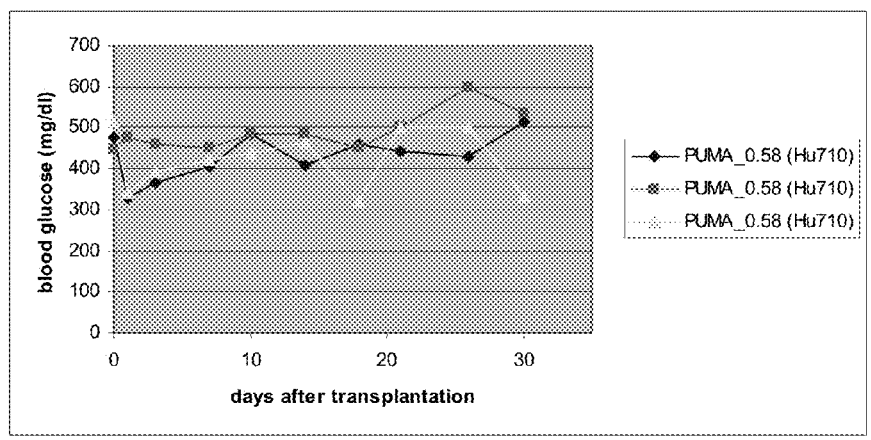
Figure 5G:
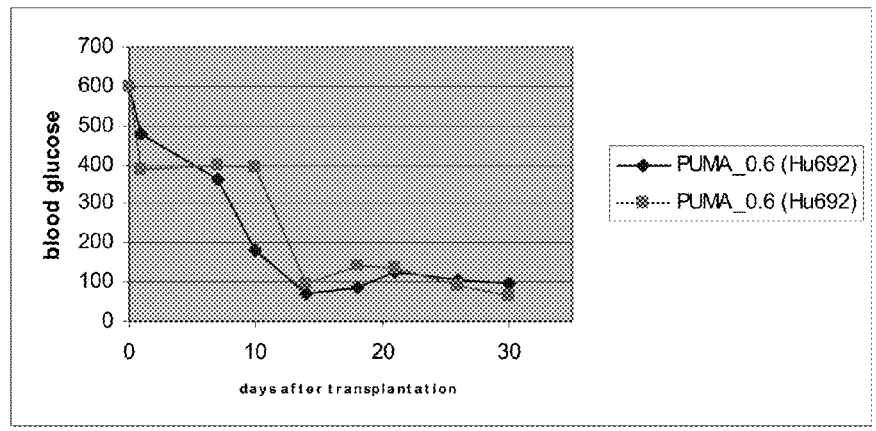
Figure 5H:
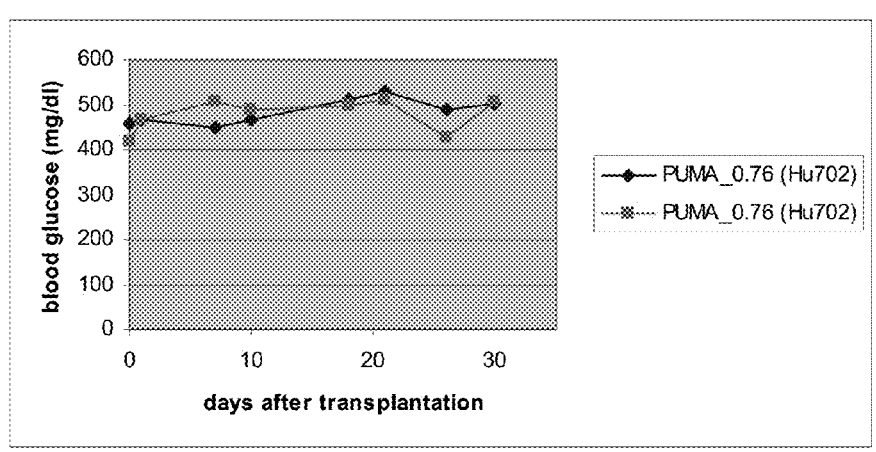
Figure 5I:
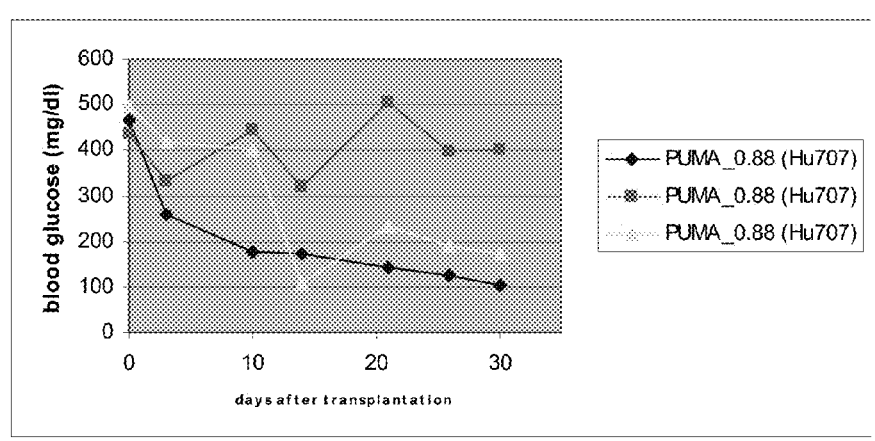
Figure 5J:
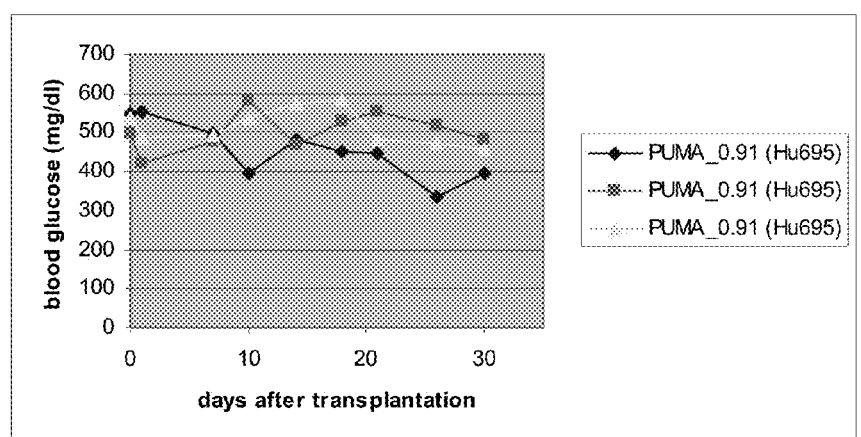

TNF-α may decrease glucose-induced insulin secretion in a β cell line before a measurable change in cell viability can be detected because a decrease in cell function occurs before a decrease in cell viability. TNF-α also abolishes glucose stimulated preproinsulin mRNA synthesis. This inhibition was inversely related to the up regulation of PUMA by TNF-α and/or IFNγ (FIG. 2A and FIG. 3C). Based on these observations, PUMA can be used as a marker to assess TNF-α induced β cell stress expressed as the inhibition of preproinsulin synthesis and apoptosis. As shown in FIG. 4, pre-incubation of islets with Etanercept successfully inhibited PUMA, IL-8 and TNF expression confirming that the effect of recombinant TNF-α added to the culture media was absorbed by Etanercept as expected.

A recent experiment reported a pilot randomized trial of Etanercept treatment in children with new onset of T1DM resulted in lowering $HbA_1C$ levels and increased levels of endogenous insulin production, suggesting the preservation of β cell function. Imatinib, a tyrosine kinase inhibitor that suppresses NF-κB activation, is shown to protect islets from combined cytokines in vitro and prevents the spontaneous onset of diabetes in NOD mice. JAK inhibitor also suppressed PUMA expression caused by TNF-α stimulation. JAK inhibitor is effective for prevention of islet cell death and development of diabetes in animal models. These lines of evidence support the usefulness of PUMA, IL-8, and TNF-α mRNA expression analysis along with preproinsulin mRNA synthesis to confirm the effectiveness of drugs for protecting human islets from apoptosis before conducting clinical trials. These markers also can be used in the discovery of compounds that protect islets from TNF-α damage. See FIGS. 4-7.

Compositions containing anti-PUMA molecules or PUMA antagonists are contemplated for the reduction of PUMA and/or PUMA expression, which in turn, increases islet cell health. Such compositions comprising an anti-PUMA molecule as described herein preferably contain a pharmaceutically acceptable excipient, diluent or carrier.

A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., 7th ed., Lippincott, Williams, & Wilkins; and Handbook of Pharmaceutical Excipients (2000) A. H. Kibbe et al., 3rd ed. Amer. Pharmaceutical Assoc. Such carriers can be formulated by conventional methods and can be administered to the subject at a suitable dose. Administration of the suitable compositions may be effected by different ways, e.g. by intravenous, intraperitoneal, subcutaneous, intramuscular, topical or intradermal administration. The route of administration, of course, depends, inter alia, on the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of condition or disease, general health and other drugs being administered concurrently.

There may also be situations in which it is desirable to harm or kill islet cells, such as when the cells are already unhealthy or have over-proliferated. In such instances PUMA itself or a PUMA agonist may be administered to the cells as an apoptotic agent. Care must be taken to target only the islet cells that are desired to be killed and so highly targeted approaches are preferred for in vivo administration. Because of this fact, assays and methods of administering PUMA to islet cells for its apoptotic properties may be better suited to in vitro applications.

PUMA levels may be measured by any accurate means including the means disclosed in the following experimental examples, in vitro, or in vivo using either biological samples or non-invasive techniques, such as functional MRI. Methods of multivariate analysis of the data that may be used in for analysis in the present assays and methods include but are not limited to: multivariate analysis of variance, principal component analysis, factor analysis, canonical correlation analysis, redundancy analysis, correspondence analysis, multidimensional scaling, discriminant function, linear discriminant analysis, clustering systems, and artificial neural networks. Base levels of PUMA expression are only a guide as individual cells and organs may vary.

Methods

The following reagents and antibodies were used in the present experiments: Reverse Transcriptase: Promega (San Luis Obispo, Calif.), SYBER Green Mix: Bio-Rad (Hercules, Calif.), Recombinant human TNF-α, recombinant human IFNγ, recombinant rat TNF-α, and recombinant rat IFNγ: R&D Systems (Minneapolis, Minn.), Antibodies for Phospho p65 (Ser536) and β actin: Cell Signaling Technology (Danvers, Mass.), PUMA antibody: Abcam (Cambridge, Mass.), BAY11-7082: Calbiochem (San Diego, Calif.), Guinea pig anti-human insulin primary antibody: DAKO (Carpinteria, Calif.), Cy5-conjugated secondary antibody: Jackson Immuno-Research (West Grove, Pa.), 4'-6-Diamidino-2-phenylindole (DAPI) and streptozotocin: Sigma-Aldrich (St. Louis, Mo.), ON-TARGETplus® siRNA Reagents: Dharmacon, Inc. (Lafayette, Colo.), TRI Reagent: Molecular Research Center Inc. (Cincinnati, Ohio), tetramethylrhodamine, ethyl ester, perchlorate (TMRE): Invitrogen (Carlsbad, Calif.), APC Annexin V: BD Biosciences (San Jose, Calif.), Caspase-9, Cleaved caspase-8, Cleaved caspase-3, β-actin, anti-rabbit IgG HRP-linked Antibody, LumiGLO® chemiluminescent substrate: Cell Signaling Technology (Danvers, Mass.), western blot Cytochrome c oxidase subunit IV: Cox IV, PUMA: Cell Signaling Technology.

Human Islet and Acinar Cell Culture:

Human islets and acinar cells isolated for research use were obtained from the Southern California Islet Cell Resources (SC-ICR) Center, Beckman Research Institute of the City of Hope (Duarte, Calif.) 1 to 3 days after isolation. The donor age ranged from 18 to 67 (48±14) years and included both sexes. Islet preparations with >70% purity and >90% viability were used. The use of human islets and acinar cells in this study was approved by the Institutional Review Board of the City of Hope. For mRNA experiments, islets between 150 μm to 300 μm in diameter (medium size islet) were handpicked in hexiplicate by experienced personnel under a dissection microscope without staining. Each handpicked islet was cultured individually in a non-tissue culture treated 96 well plate (Sarstedt, Newton, N.C.) with a CMRL (Mediatech Inc., Holly Hill, Fla.) based serum-free medium, which is used to culture human islets for clinical transplantation. Islets were treated with or without recombinant human TNF-α (0, 1, 5, 50 ng/mL) and/or recombinant human IFNγ (0, 10, 100, 1000 U/mL) for up to 16 hours. For other islet experiments, 500 to 1000 islet equivalent (IEQ) were cultured (500 IEQ/mL of medium) in a Petri dish for up to 24 hours in the same condition described above unless otherwise specified. For acinar cell experiments, acinar cells were kept in islet culture medium at 4° C. immediately after the isolation and used within 24 hours. Aliquots of 5-10 acinar cell clusters in triplicates were cultured with islet culture medium with or without TNF-α for up to 16 hours. For drug compound screening experiments, islets were pre-incubated with Etanercept, FK506, Cyclosporine (CsA), Rapamycin, Imatinib mesylate, Janus Kinase (JAK) inhibitor or p38 inhibitor, SB203580, for 1 hour, and then 5 ng/mL TNF-α was added to the islet culture for 4 hours. All the compounds except Etanercept (0.1 μg/mL) were dissolved in dimethyl sulfoxide (DMSO) and used at a concentration of 10 μM (all compounds are gifts from Hitachi Chemical Research Center).

Quantification of mRNA from a Single Islet:

RNA purification and PCR was performed as described previously (32). Briefly, following culture, islets were transferred to a 96-well filter plate (Hitachi Chemical Research Center-HCR, Irvine, Calif.) (44) and 50 μL of Lysis Buffer (HCR) containing a cocktail of specific reverse primers was applied to each well. Poly(A)+ mRNA isolation was performed using the Hem(A)+™ System (Hitachi Chemical Research Center, Irvine, Calif.). The resultant cell lysates were transferred to oligo(dT)-immobilized microplates (GenePlate, HCR) for poly(A)+ mRNA purification (45). The cDNA was directly synthesized with 30 μL of solution in each well: specific primer-primed cDNA in the liquid phase and oligo(dT)-primed cDNA in the solid phase (44). The cDNA in the solution was diluted by adding 30 μL nuclease-free water, with 4 μL of the diluted cDNA used for SYBR Green PCR (BioRad, Hercules, Calif.) (46). Each gene was amplified individually. The cycle threshold (Ct) was determined using analytical software (SDS, Applied Biosystems, Foster City, Calif.). Differences in Ct between the target and control mRNA (ΔCt) are used to quantify the relative amount of each target, calculated as $2^{-\Delta Ct}$. Primers used for the gene expression assays are described previously (32, 36, 47, 48).

Measurement of Preproinsulin mRNA (or Precursor mRNA) Synthesis and Total Insulin Release:

Hand picked human islets were cultured with 100 uL of RPMI 1640 medium containing 5% fetal bovine serum and either low-glucose (3.3 mmol/L) or high-glucose (17 mmol/L) for 16 hours. Preproinsulin mRNA synthesis was measured from the islets by the methods described above. Pre-spliced preproinsulin mRNA (preproinsulin precursor mRNA) was normalized by pre- and post-spliced preproinsulin mRNA as described previously (32). Specifically, primer pairs used to perform qRT-PCR of pre-spliced preproinsulin mRNA are as follows: AGGTGGGCTCAGGAT-TCCA (SEQ ID NO.1) (In1 upstream) and TCACCCCCA-CATGCTTCAC (SEQ ID NO.2) (In1 downstream); ACTCGCCCCTCAAACAAATG (SEQ ID NO.3) (In2 upstream) and TGAATCTGCGGTCATCAAATG (SEQ ID NO.4) (In2 downstream); CTCTGCCTCGCCGCTGTTC (SEQ ID NO.5) (In2Ex3 upstream) and TCCACAATGC-CACGCTTCTG (SEQ ID NO.6) (In2Ex3 downstream); GCAGCCTTTGTGAACCAACA (SEQ ID NO.7) (Ex2a upstream) and TTCCCCGCACACTAGGTAGAGA (SEQ ID NO.8) (Ex2a downstream); GGGAACGAGGCTTCT-TCTACAC (SEQ ID NO.9) (Ex2b upstream) and CCA-CAATGCCACGCTTCTG (SEQ ID NO.10) (Ex2b downstream); and CATTGTGGAACAATGCTGTACCA (SEQ ID NO.11) (Ex3 upstream) and GCCTGCGGGCT-GCGTCTA (SEQ ID NO.12) (Ex3 downstream). The culture supernatant was collected from each well after 16 hour-culture to measure insulin contents using an Enzyme-Linked ImmunoSorbent Assay (ELISA) kit for human insulin (Mercodia Inc., Winston Salem, N.C.) following the manufacturer's protocol.

Western Blot:

Five hundred IEQ samples were harvested before and 24 hours after culture with or without TNF-α and/or IFNγ, washed twice with ice cold phosphate buffered saline (PBS), and stored at −80° C. until use. In some experiments, islets were pre-incubated with 10 μM NFκB inhibitor; BAY11-

7082 for 1 hour before cytokine stimulation. Islet cell lysis and western blot was performed as previously described (49).

β Cell Apoptosis Analyzed by Laser Scanning Cytometry (LSC):

Islet paraffin sections were stained for terminal uridine deoxynucleotidyl transferase dUTP nick end labeling (TUNEL) using the Apop Tag plus Fluorescein In Situ Apoptosis Detection Kit (Chemicon, Temecula, Calif.) followed by immunostaining for insulin using a guinea pig anti-human insulin primary antibody and a Cy5-conjugated secondary antibody. All sections were counterstained for DNA with DAPI. To evaluate β cell apoptosis, slides were scanned using the iCys laser scanning cytometer and the iCys 3.2.5 software (Compucyte, Cambridge, Mass.) as previously described (50). Cells co-staining for insulin and TUNEL were designated as apoptotic β cells and their percentage was obtained from the histogram. The percentage of apoptotic β cells was calculated by dividing the insulin/TUNEL double-positive cell number by the total number of insulin-positive cells.

siRNA Transfection and Flow Cytometry Analysis:

PUMA siRNA containing 4 individual siRNA targeting PUMA and negative control siRNA were transfected into INS-1 cells at a 20 nM concentration. Transfection was performed using ON-TARGETplus® siRNA reagents according to the manufacturer's instructions. INS-1 cells were cultured in RPMI 1640 medium containing 5% fetal bovine serum and 15 mM HEPES. Recombinant rat TNF-α (50 ng/ml) and/or recombinant rat IFNγ (1000 U/ml) were added in the culture media 24 hours after the transfection and cultured for additional up to 48 hours. Cultured cells were harvested using TRYPLE™ (Invitrogen, Carlsbad, Calif.) for flow cytometric (FCM) analysis performed on a CYAN™ ADP Analyzer (Beckman Coulter, Fullerton, Calif.). The transfection rate as confirmed by a transfection indicator labeled with 6-FAM™ was more than 75%. To assess mitochondrial membrane permeability, cell were incubated with 100 nM TMRE in culture media for 30 minutes and then washed with PBS twice before the analysis. Cell death was analyzed by staining with 1 μg/ml of DAPI.

Assessment of In Vivo Islet Function in Diabetic NOD-scid Mice:

Male NODscid mice, ages 10-12 weeks, were obtained from the Animal Resources Center of Beckman Research Institute of the City of Hope and used as human islet recipients. Mice were rendered diabetic by intraperitoneal injection of 50 mg/kg streptozotocin (STZ) on three consecutive days. Those that exhibited hyperglycemia (>350 mg/dL) for two consecutive days were used as recipients. 1200 IEQ islets were transplanted under the left kidney capsule of diabetic mice. Blood glucose levels were measured 2-3 times weekly. Recipient mice that maintained a blood glucose <200 mg/dL were considered to have reversed diabetes. At the end of each experiment, a left nephrectomy was performed to confirm graft dependence. In separate experiments, islets were isolated from male Lewis rats weighing 250-350 g (Charles River Laboratories) using our standard procedure (39) and 250 hand-picked islets transfected with either PUMA siRNA or Control siRNA were transplanted into the liver of diabetic NODscid mice via the portal vein. All the animal procedures followed protocols approved by the Institutional Animal Care and Use Committee of the City of Hope/Beckman Research Institute.

Statistical Analysis:

Data are presented as a mean±standard error. Paired two-tailed Student's t-test was used to compare the difference between the two groups. The Correlation and Analysis of variance procedures were applied to assess the strength of linear dependence between two variables (correlation coefficient: r). P value of less than 0.05 was considered significant.

Results

Figure 1:
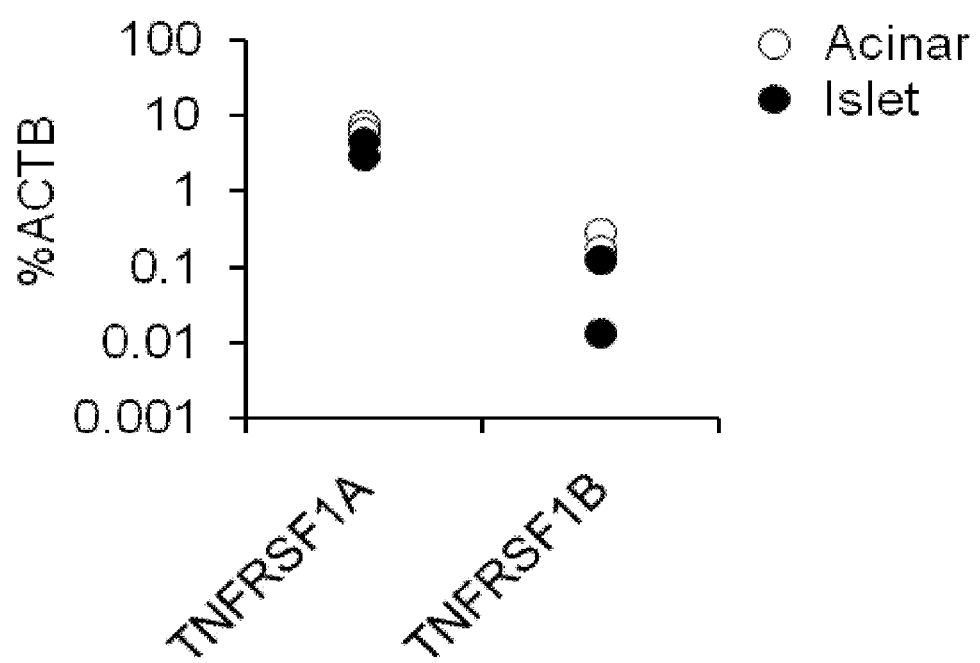
FIG. 1. TNFRSF mRNA expression was examined in human islets (in which cDNA was obtained from 10 islets) as well as in acinar cells. Among two TNF-α receptors, TNFRSF1A was expressed at a very high level, while the other receptor, TNFRSF1B was detectable but very low in human islets. Differences in cycle threshold (Ct) between the target and β actin (ACTB) gene (ΔCt) were used to quantify the relative amount of each target, calculated as $2^{-\Delta ct}$ and the expression level was shown as % ACTB.

Human Islets Express PUMA mRNA by TNF-α Stimulation:

The expression of TNFRSF in human islets was previously. TNFRSF gene expression was examined in isolated human islet and acinar cells. Both islet and acinar cells have a similar pattern of TNFRSF expression (FIG. 1). One of the abundant receptors in human islets was TNFSF1A, the receptor for TNF-α, while TNFSF1B, another receptor for TNF-α, was detectable but at a low level (FIG. 1).

Figure 8A:
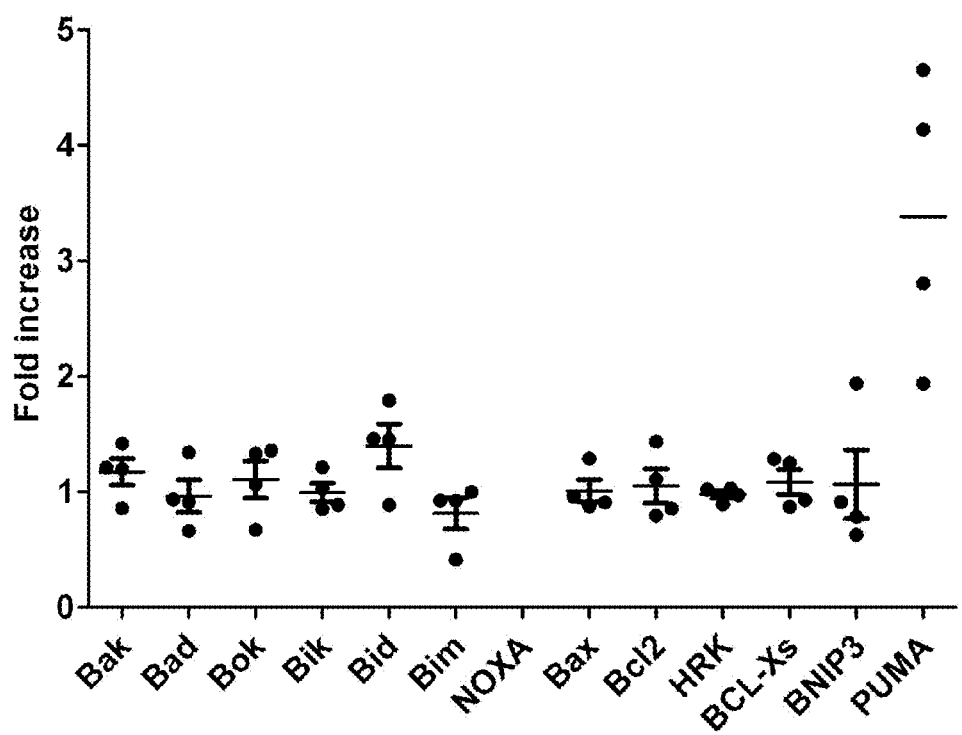
FIG. 8. TNF-α induces PUMA expression in human islets and acinar cells. A) TNF-α induced Bcl-2 family mRNA in islets. Single islets were stimulated with or without 50 ng/ml TNF-α for 16 hours. Each dot indicates the result of one islet lot tested in hextuplicate. The tests were performed using 4 different human islet lots. Bars indicate the mean of 4 lots. Each gene expression was normalized by ACTB (a gene encoding β actin), and the fold increase was calculated by dividing TNF-α treated islets by control islets (*p<0.01, n=4). PUMA mRNA was by far the most significantly TNF-α induced member of the Blc-2 family members.
FIGS. 8B-D) PUMA (FIG. 8B), IL-8 (FIG. 8C) and TNF-α (FIG. 8D) expression from single human islets (n=6) stimulated with 0 (open circles), 1 (solid triangles), 5 (solid squares) and 50 ng/ml (solid circles) TNF-α for 0, 1, 4, 16 hours in 3 independent cases. Dose dependent expression of E) PUMA, F) IL-8 and G) TNF-α in human islet at the 4 hour time point (n=3). The PUMA expression in human islets was elevated by TNF-α as early as one hour, increased during the next 4 hours, and maintained at the similar level for 16 hours. Along with PUMA, interleukin-8 (IL-8) and endogenous TNF mRNA expression also increased by TNF-α in islet in a time and dose dependent manner. H) PUMA, I) IL-8 and J) TNF-αmRNA expression in acinar cells, in triplicate, stimulated with 0 (open circles), 1 (solid triangles), 5 (solid squares) and 50 (solid circles) ng/ml TNF-α for 0, 1, 4, 16 hours. Representative data from two independent cases is shown. K) PUMA and L) IL-8 expression in human islets stimulated with or without TNF-α (1, 5, 50 ng/ml) and/or IFNγ (10, 100, 1000 U/ml) for 4 hours. When combined with TNF-α, IFNγ strongly augmented TNF-α mediated PUMA expression. PUMA expression is highest for TNF-α at 50 ng/ml+IFNγ at 1000 U/ml. Results show representative data from 3 cases (with statistical significance indicated as *p<0.05 [one asterisk] or **p<0.001 [two asterisks] as compared to control; p<0.01 as compared to TNF-α at 50 ng/ml; no asterisks indicates a lack of statistical significance). All data are presented as a mean±standard error. The expression of PUMA, IL-8 and TNF also increased in acinar cells. However, unlike in the islets, the expression of PUMA and IL-8 reached to the peak level by 4 hours and decreased to the basal level by 16 hours.

In order to examine whether TNF-α stimulation of human islets interacts with the intrinsic pathway and induces cell death, islets were stimulated with recombinant human TNF-α protein (50 ng/mL) for 16 hours and apoptosis-related Bcl-2 family genes were examined. As shown in FIG. 8A, TNF-α induced higher levels of PUMA as compared to non-stimulated controls (1.9-4.7 fold), whereas the increases in other Bcl-2 family mRNAs were all less than 2 fold (n=4). Three of the 4 TNF-α stimulated islet samples also showed elevated induction of BID, but at levels far less than those of PUMA.

Figure 8B:
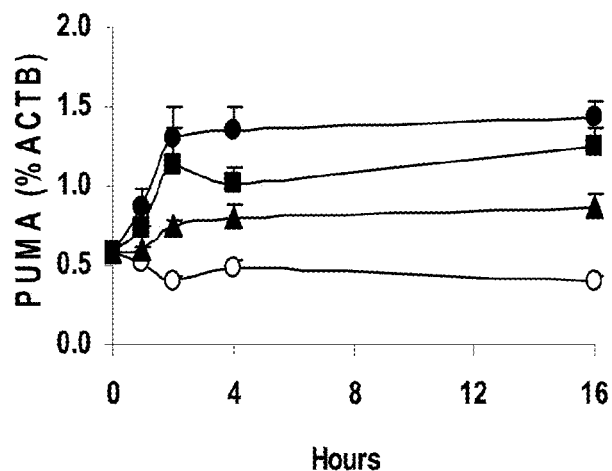
Figure 8C:
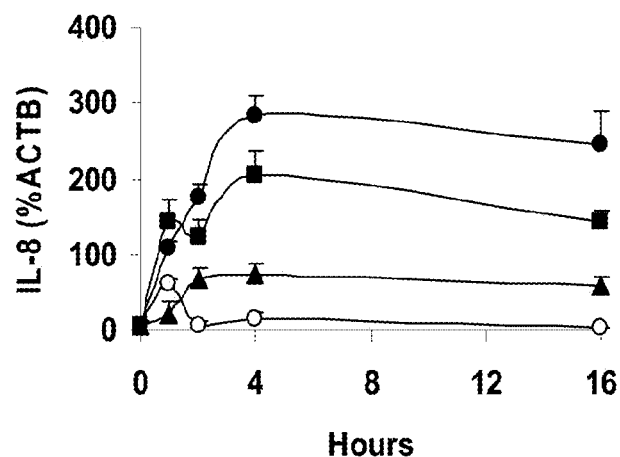
Figure 8D:
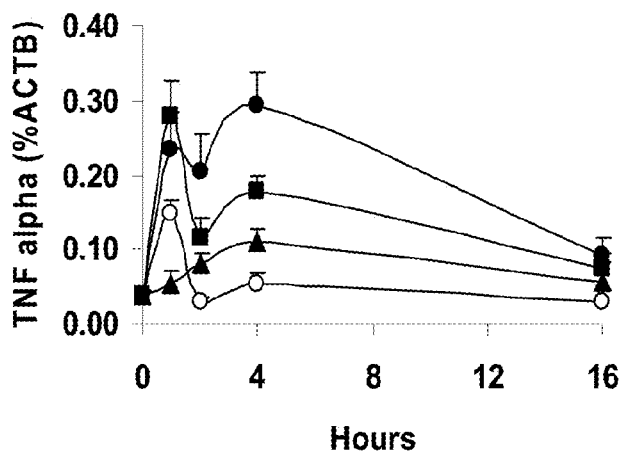
Figure 8E:
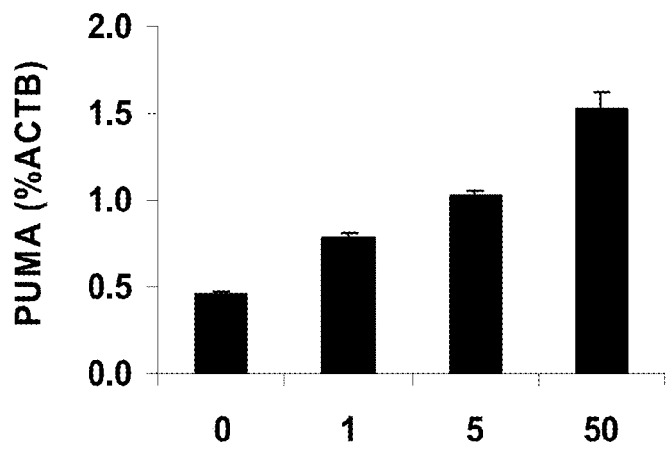
Figure 8F:
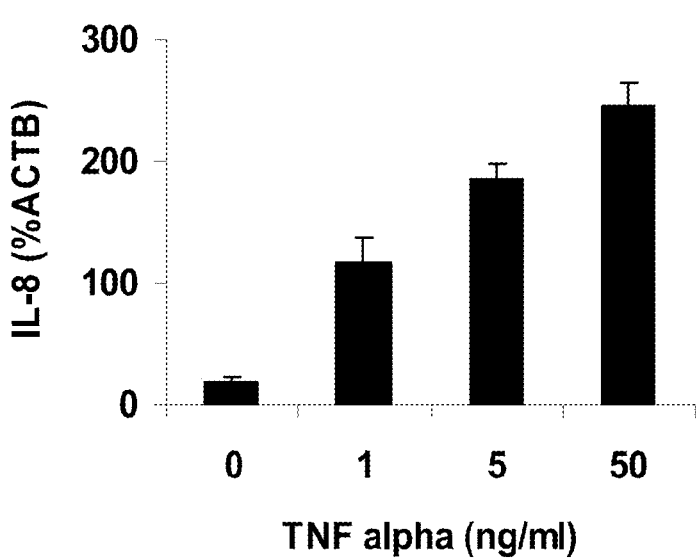
Figure 8G:
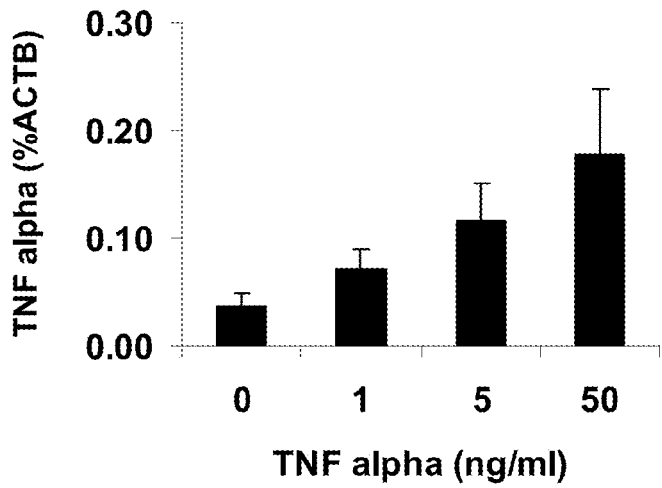

PUMA expression was elevated as early as one hour after the exposure to TNF-α, increasing during the next 4 hours, and maintained at a similar level for 16 hours (FIG. 8B). The expression of PUMA was TNF-α dose dependent (FIG. 8E). Along with PUMA, interleukin-8 (IL-8) mRNA expression also increased in TNF-α stimulated islets in a time and dose dependent manner (FIG. 8C, 8F). Additionally, stimulation of human islets with recombinant TNF-α was found to induce TNF mRNA expression in the islet cells (FIGS. 8D and 8G), indicating the existence of a possible positive feedback mechanism.

Figure 8H:
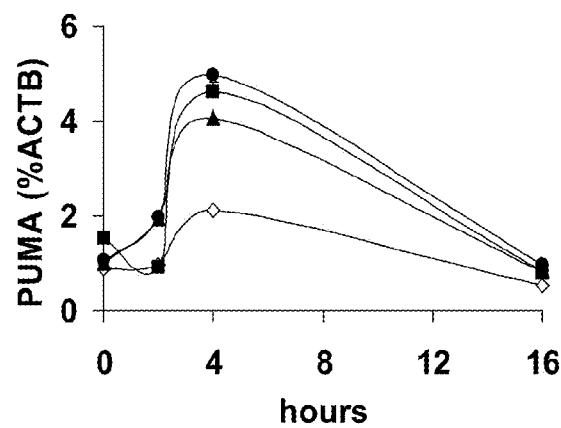
Figure 8I:
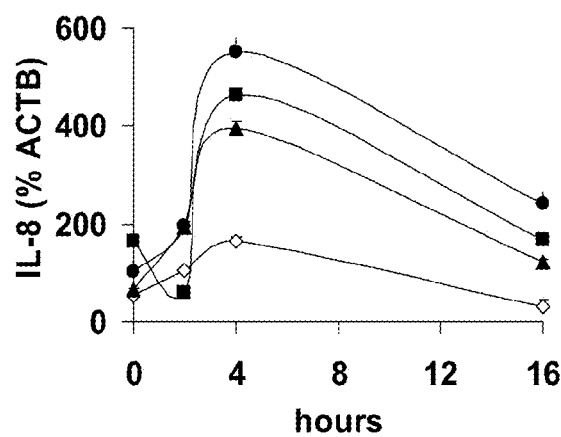
Figure 8J:
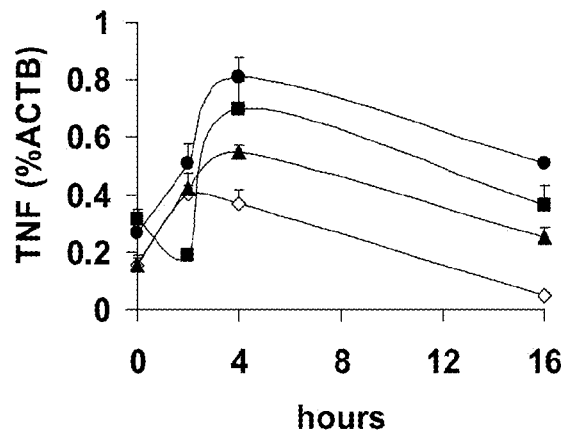

To examine whether the PUMA up regulation in response to TNF-α was islet specific, acinar cells isolated from human pancreata were also stimulated with TNF-α. The expression of PUMA, IL-8 and TNF was increased in acinar cells, however, the expression reached peak levels by 4 hours and decreased to basal levels by 16 hours (FIGS. 8H, 8I, and 8J).

Pancreatic tissues, including islets and acinar cells, are known to contain passenger leukocytes, which may be the source of the PUMA, IL-8 and TNF expression detected above. To show that this expression was not due to passenger leukocytes, TNF-α-mediated PUMA expression was examined in blood leukocytes. TNF-α alone, even with higher doses than that used in islets (200 ng/mL), did not induce PUMA in leukocytes. In contrast, leukocytes did express a high level of IL-8 following TNF-α stimulation. These results show that passenger leukocytes in islets did not contribute to the TNF-α-mediated PUMA expression by islets (FIG. 9).

PUMA is known to be up regulated by p53, either dependent or independent manner. To test the involvement of p53 in the PUMA expression by pancreatic cells, the expression of p21/CDKN1A (cyclin-dependent kinase inhibitor 1A), the major transcriptional target of the p53 tumor suppressor protein, was examined in both islets and acinar cells. Up regulation of CDKN1A was not detected in either islets or acinar cells, which indicates that the PUMA induction in islets and acinar cells by TNF-α stimulation was possibly p53 independent, or at least independent of p21.

Figure 8K:
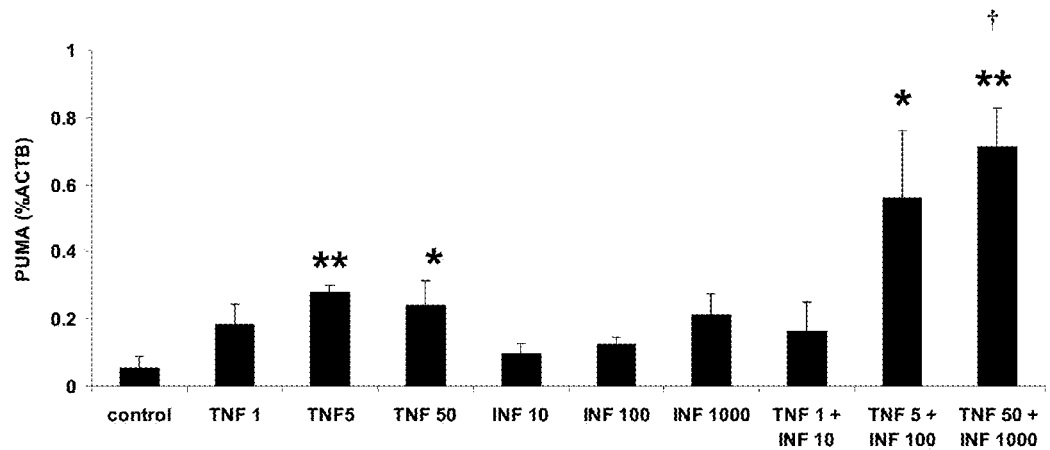
Figure 8L:
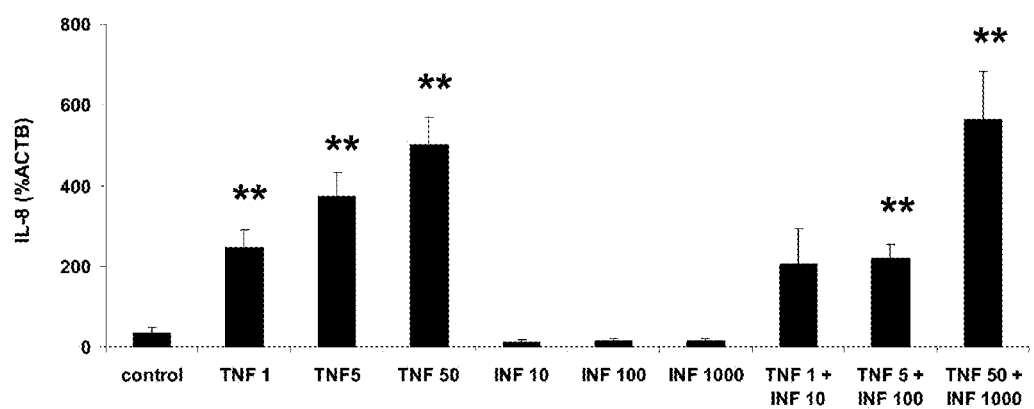

PUMA expression by human islets stimulated by recombinant human IFN-γ alone or in combination with TNF-α was compared. As shown in FIG. 8K, IFN-γalone did not induce PUMA, whereas the combination of TNF-α and IFN-γ strongly augmented PUMA expression in the islets. Similarly, IFN-γ alone did not induce IL-8 expression which was increased by combining with TNF-α (FIG. 8L).

PUMA is Translationally UP Regulated in Human Islets Through NFκB Activation:

Translation of PUMA induced by TNF-α alone or in combination with IFN-γ into PUMA protein was examined. Islets were stimulated in culture for 16 hours with TNF-α alone or together with IFN-γ, lysed and analyzed by western blot. The expression of PUMA was significantly increased by TNF-α alone at a concentration of 50 ng/mL (p<0.05) and the combination of TNF-α and IFN-γ (p<0.005), but not by IFN-γ (1000 U/mL) alone (FIG. 2A). This observation is consistent with mRNA expression results.

Figure 2B:
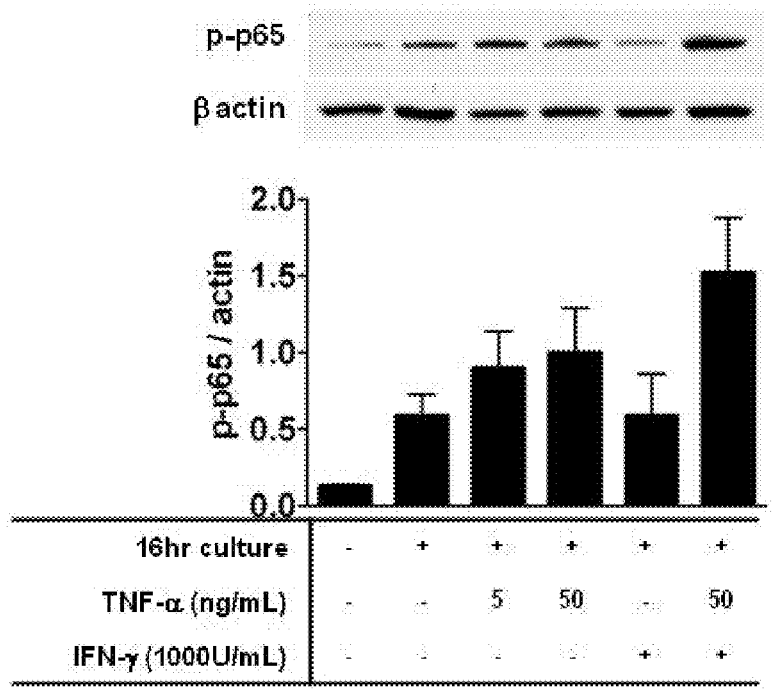
Figure 2C:
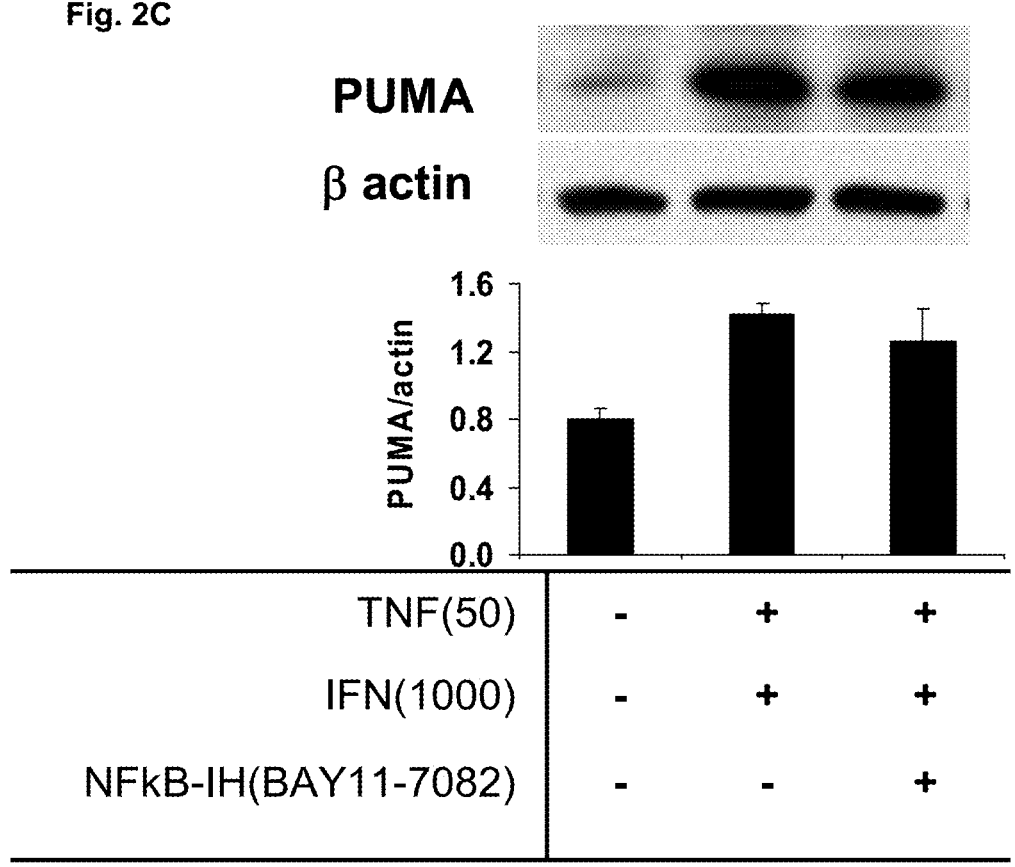
Figure 2D:
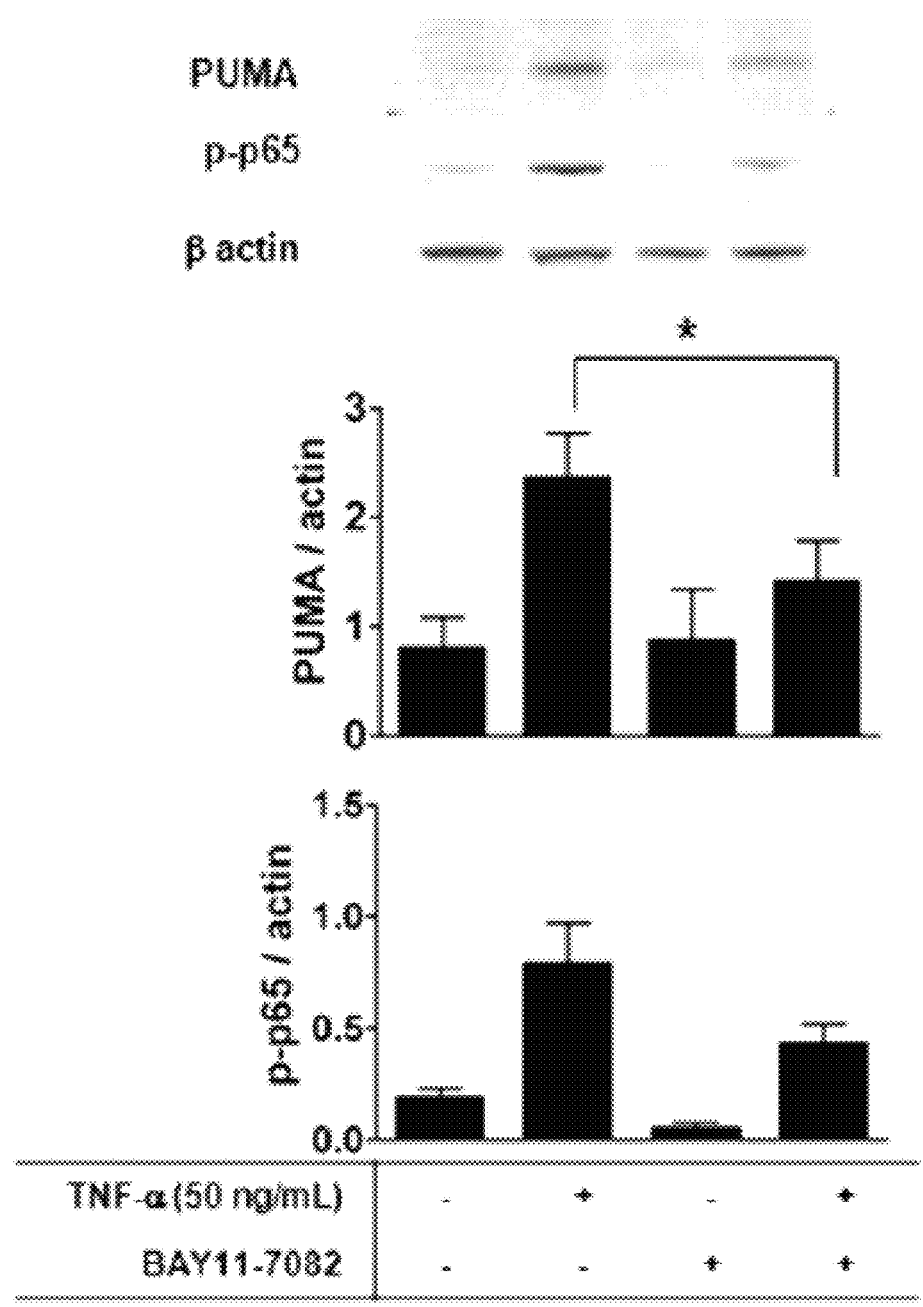

The p65 component of NFκ directly binds to the κB site of the PUMA promoter region driving transcriptional activation in response to TNF-α stimulation. The up regulation of PUMA in human islets is regulated by NFκB activation. Increased phosphorylation of p65 protein was detected in the islets stimulated by TNF-α but not IFN-γ. The expression of p65 is further increased by stimulation with both TNF-α and IFN-γ (FIG. 2B). Although PUMA expression in TNF-α stimulated islets increased in response to NFκB activation, the NFκB inhibitor BAY11-7082 did not inhibit PUMA expression induced by the combination of TNF-α and IFNγ (FIG. 2C).

Figure 10:
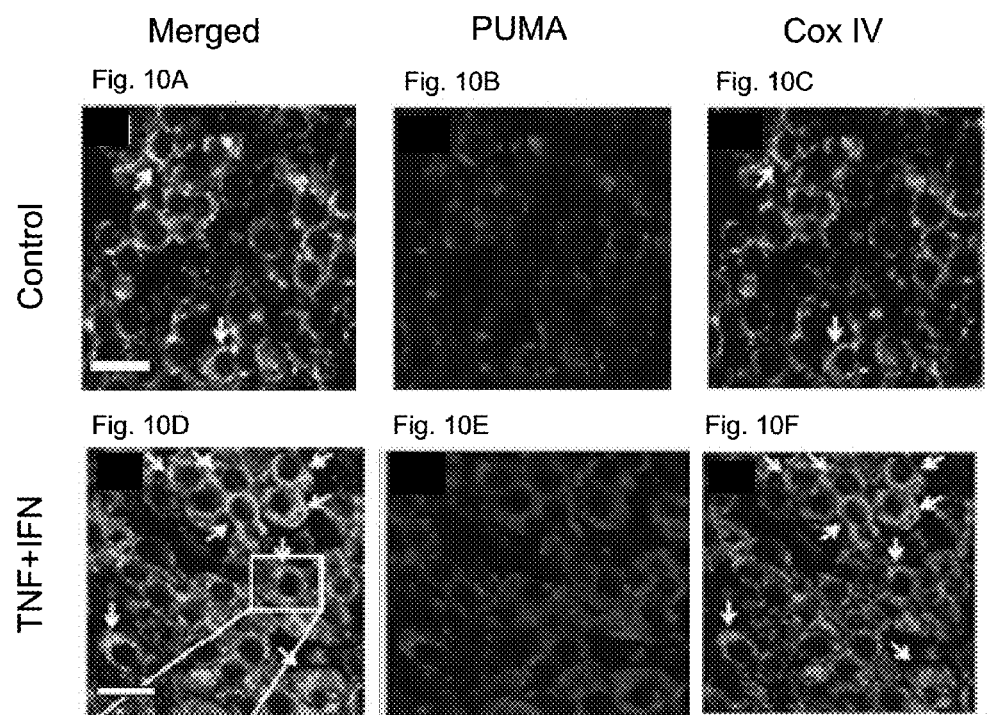
FIG. 10. TNF-α+IFN-γ induced up-regulation of PUMA and clustering of mitochondria in cytoplasm of human β-cells. Paraffin sections of human islets cultured with TNF-α (50 ng/ml)+IFNγ (1000 IU/ml) or without (control) for 24 hours were stained for PUMA, Cox IV and insulin (data not shown); medium alone or with TNF-α+IFN-γ.
Figure 10:
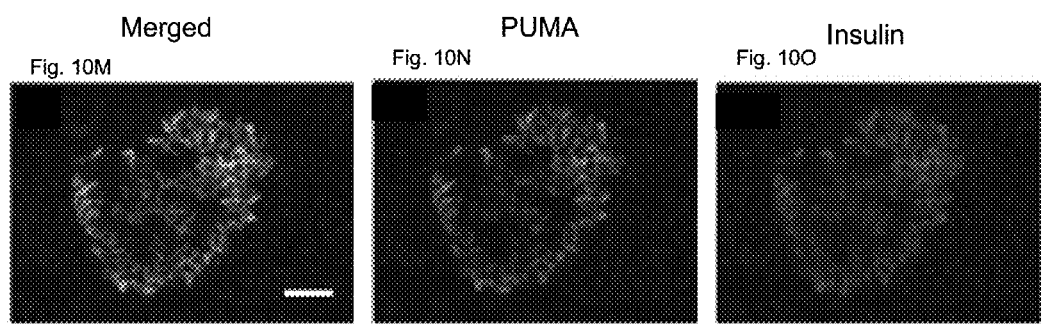
Figure 10:
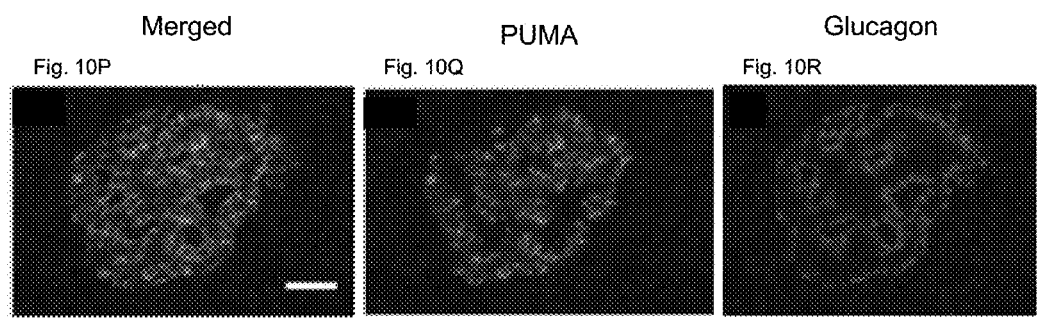

Treatment of human islets with TNF-α and IFN-γ together induced mitochondrial clustering and increased PUMA protein in beta-cell cytoplasm: Confocal microscopy was used to examine PUMA expression in human islets treated with TNF-α+IFN-γ for 24 hours. Paraffin sections of the islets were stained for PUMA, Cox IV (marker for mitochondria) and insulin. PUMA expression was up-regulated in TNF-α+IFN-γ treated islets (FIGS. 10B and 10E). The treatment also increased mitochondrial condensation and perinuclear clustering as shown by Cox IV staining (arrows in control (FIGS. 10A and 10C) as compared to TNF-α+IFN-γ treated cells (FIGS. 10D and 10F)). Higher PUMA expression in the cytoplasm was associated with morphological changes and cellular redistribution of mitochondria. The co-localization of PUMA and Cox IV were found in cells marked by arrows in FIGS. 10A and 10D. The merged image of PUMA and Cox IV showed co-localization of some PUMA with mitochondria around the nucleus as shown in the representative cell (arrowheads in FIG. 10J). However, the majority of cytoplasmic PUMA was independent of Cox IV. FIGS. 10H and 10I confirmed that insulin staining was independent from both PUMA and Cox IV staining, respectively. To examine the PUMA protein expression in minimally manipulated pancreatic cells, paraffin sections of pancreas tissue taken from cold preserved pancreases before islet isolation, and were stained for PUMA and insulin (FIG. 10M-O) or PUMA and glucagon (FIG. 10P-R). PUMA co-localized with beta-cells but not with alpha-cells stained for glucagon. Acinar cells surrounding islets were also negative for PUMA.

Figure 11A:
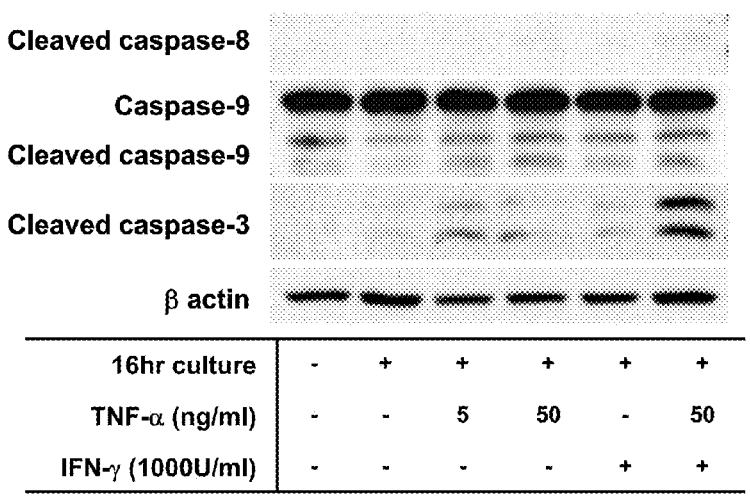
FIG. 11. TNF-α induces apoptosis through mitochondrial pathway in human islets. Silencing PUMA prevented cell death induced by TNF-α and IFNγ stimulation in INS-1 cells. A) The activation of Caspase-8, Caspase-9 and Caspase-3 was examined in islets cultured with or without TNF-α (5 and 50 ng/ml) and/or IFNγ (1000 U/ml) for 24 hours by western blot. Results show representative data from 3 cases. Paraffin sections from human islets cultured for 24 hours with or without TNF-α (50 ng/ml) (B) or the combination of TNF-α (50 ng/ml) and IFNγ (1000 U/ml) (C) were stained for TUNEL and insulin to identify apoptotic β cells, quantified using Laser Scanning Cytometry. The percentage of apoptotic β cells was calculated by dividing the TUNEL-insulin double-positive cell number by the total number of insulin-positive cells in each section (n=3, *p<0.05). β cell apoptosis was induced by TNF-α and IFNγ through activation of Caspase-9 and Caspase-3. β cell apoptosis was not detected by TUNEL staining when stimulated by TNF-α alone. However TNF induced islet apoptosis was confirmed by the increased expression of cleaved Caspase-9 and Caspase-3. PUMA siRNA or Control siRNA was transfected into INS-1 cells 48 hours before cytokine stimulation, and cultured an additional 48 hours before flow cytometric analysis. D) Percentage of dead cells assessed by % DAPI positive cells (*p<0.01, n=3). DAPI (4',6-diamidino-2-phenylindole) is a fluorescent stain that binds to DNA. E) Mitochondrial membrane permeability is assessed by TMRE staining (**p<0.005, n=3). All data are presented as a mean±standard error. F) Dot plot shows the population of DAPI positive, TMRE positive INS-1 cells transfected with siControl or siPUMA after cytokine stimulated. Representative data from 3 independent experiments. Silencing PUMA protected 13 cell from death and loss of mitochondrial membrane potential in INS-1 cells induced by TNF-α and IFNγ. G) Western blot for cleaved caspase-3 in PUMA siRNA or control siRNA transfected INS-1 cells treated with or without TNF-α (50 nq/ml) or the combination of TNF-α (50 nq/ml) and IFNγ (1000 U/ml). Data shows a representation of 4 independent experiments. H) Densitmetric quantification of the bands for the experiments shown in FIG. 11G (n=4, p<0.05).
Figure 11B:
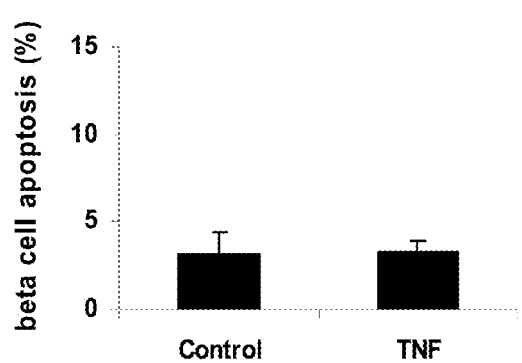
Figure 11C:
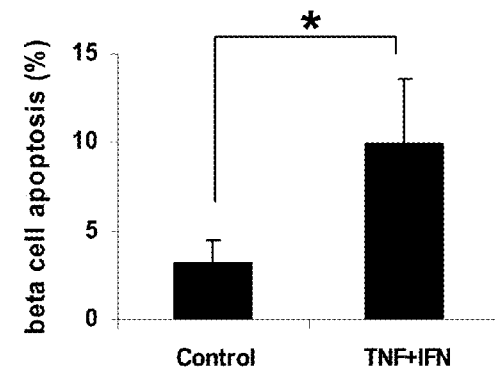

PUMA Induces Islet Cell Death Through Mitochondrial Pathway:

To examine whether islet apoptosis induced by such treatments is regulated by the extrinsic or intrinsic pathway, Caspase-8, Caspase-9 and Caspase-3 activation was determined in treated islets by western blot analysis. Caspase-9 and Caspase-3 were induced in islets treated with TNF-α alone and further increased by co-treatment with IFN-γ (FIG. 11A). In contrast, Caspase-8 was not activated in any islets, with or without TNF-α treatment. These results indicate that TNF-α induced islet cell death is primarily through the intrinsic pathway.

β cell apoptosis mediated by TNF-α or combined with IFN-γ was verified as follows: immunohistochemically stained human islets were prepared following 24-hour culture with TNF-α alone, or in combination with IFN-γ and analyzed by Laser Scanning Cytometry (LSC). Apoptotic β cells were detected by co-staining with terminal uridine deoxynucleotidyl transferase dUTP nick end labeling (TUNEL) and insulin. The percentage of apoptotic β cells was calculated as described in Methods. TNF-α treatment alone did not induce β cell apoptosis (FIG. 11B), whereas the combination of TNF-α (50 ng/mL) and IFN-γ (1000 U/mL) induced significant apoptosis of β cells (FIG. 11C).

Figure 11D:
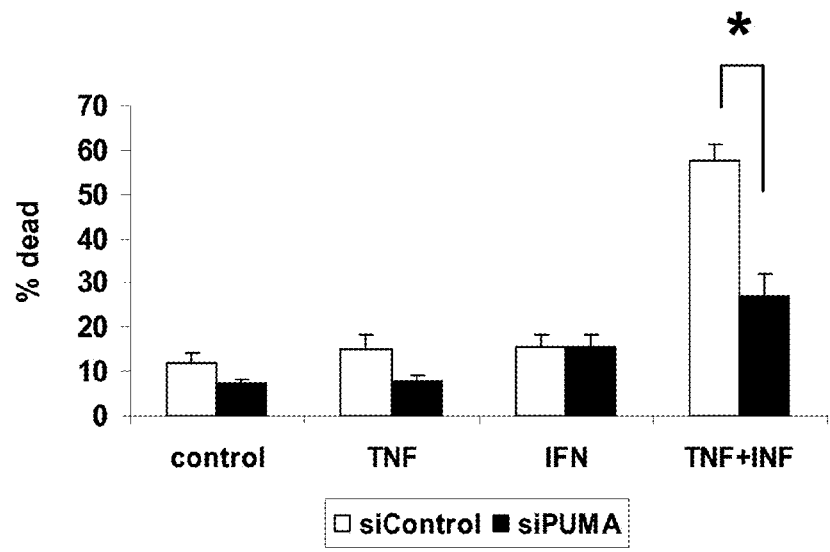
Figure 11E:
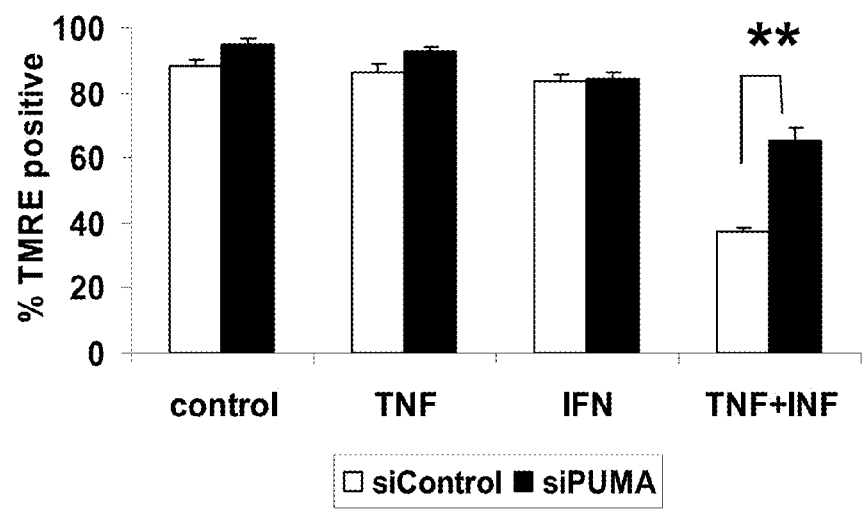
Figure 11F:
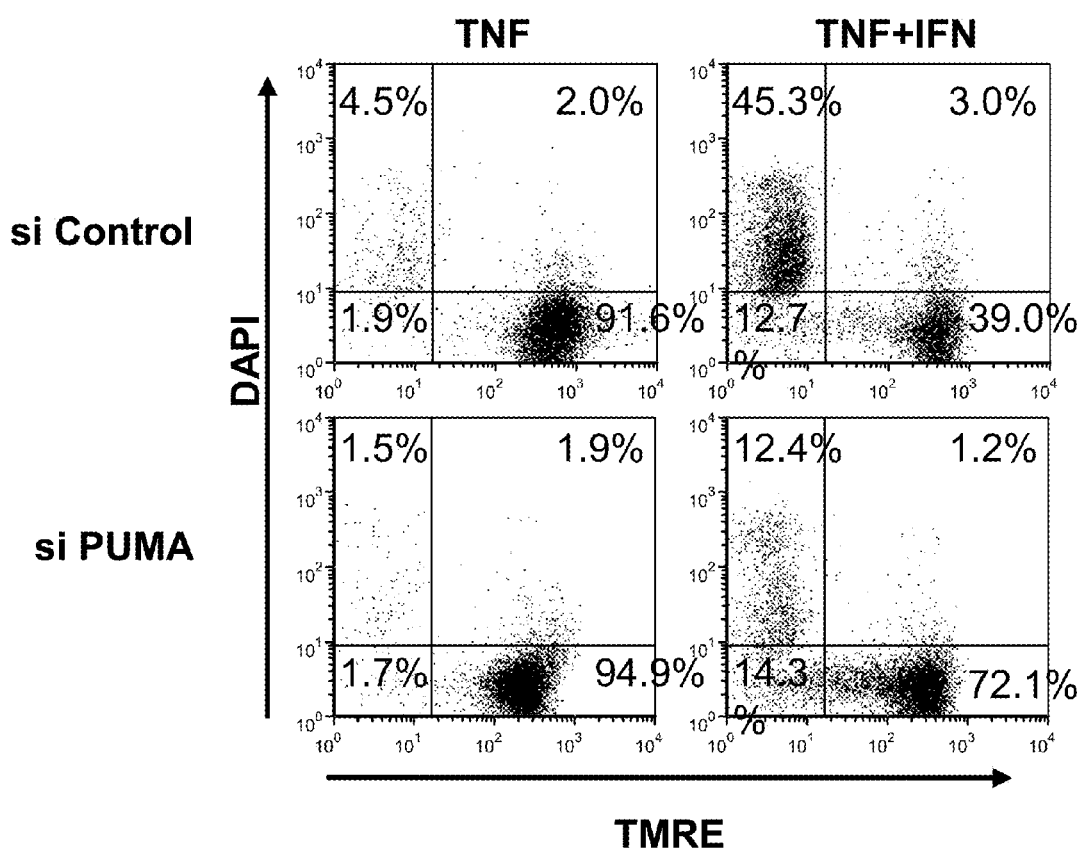
Figure 11G:
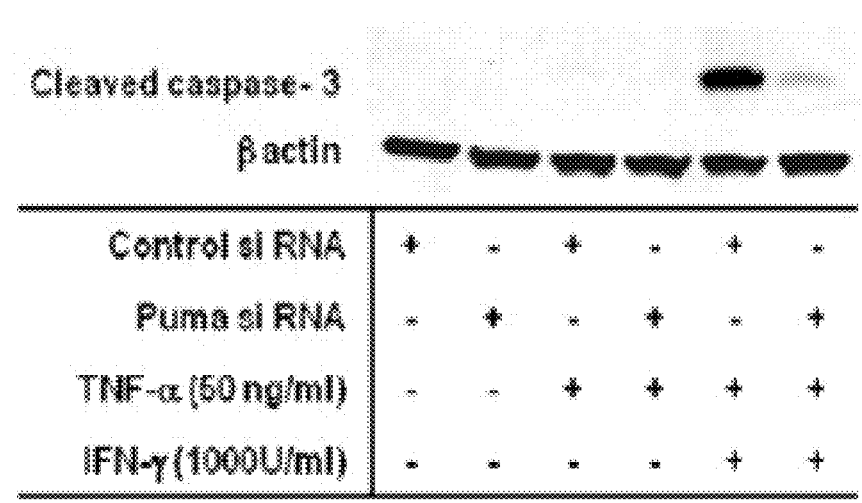
Figure 11H:
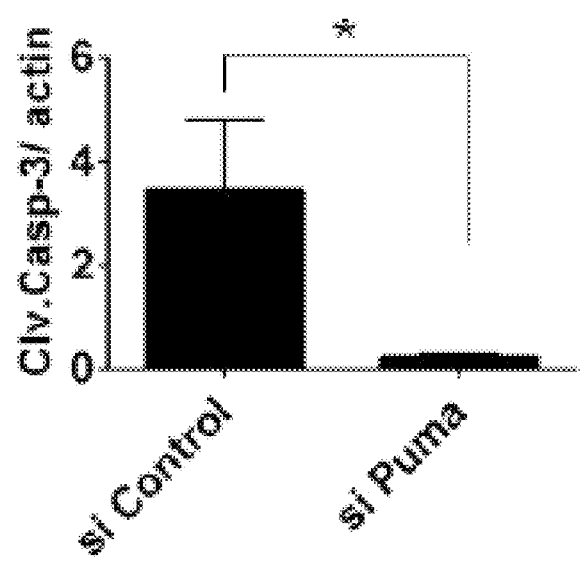

To further confirm that PUMA plays a role in TNF-α induced β cell death, PUMA siRNA was used to silence PUMA. PUMA siRNA transfection (transfection rate >80%) suppressed PUMA mRNA expression to 22.2±8.6% of the control. PUMA siRNA was transfected into the rat insulinoma cell line, INS-1, to avoid potential problems associated with transfection of human islets due to the multicellular structure. Silencing PUMA significantly reduced INS-1 cell death caused by TNF-α and IFN-γ during the 48-hour culture assessed by flow cytometric (FCM) analysis (57.7±3.6% in siControl group vs. 27.1±4.9% in siPUMA group, p<0.01) (FIG. 11D). Furthermore, INS-1 cells treated with TNF-α and INF-γ contained higher levels of TMRE positive cells when transfected with siPUMA (37.5±0.8 in siControl group vs. 65.7±3.4 in siPUMA group, n=3, p<0.005) (FIG. 11E and FIG. 11F). The presence of a higher number of tetramethylrhodamine, ethyl ester, perchlorate (TMRE) positive cells in the siPUMA group indicates that siPUMA protects the mitochondrial membrane potential and that PUMA causes cell death through mitochondrial damage. Furthermore, PUMA is required for Caspase-3 activation in response to TNF-α+IFN-γ treatment in INS-1 cells (FIGS. 11G and 11H).

Figure 3D:
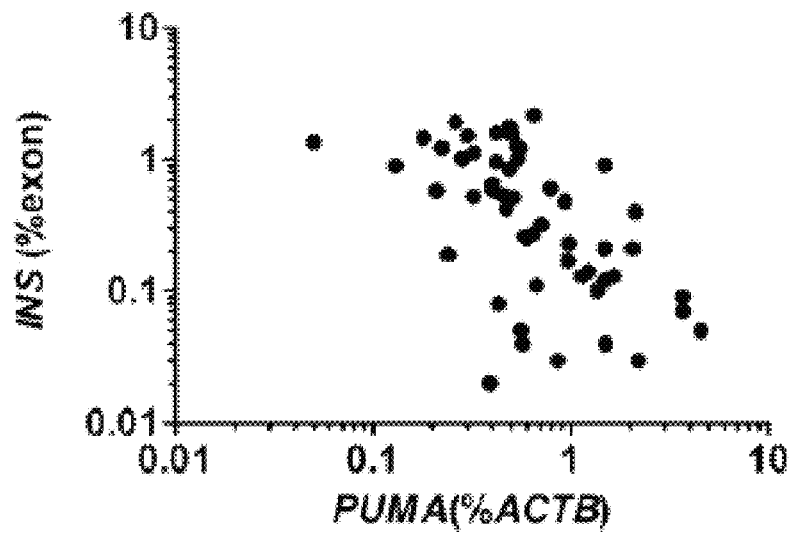
Figure 12:
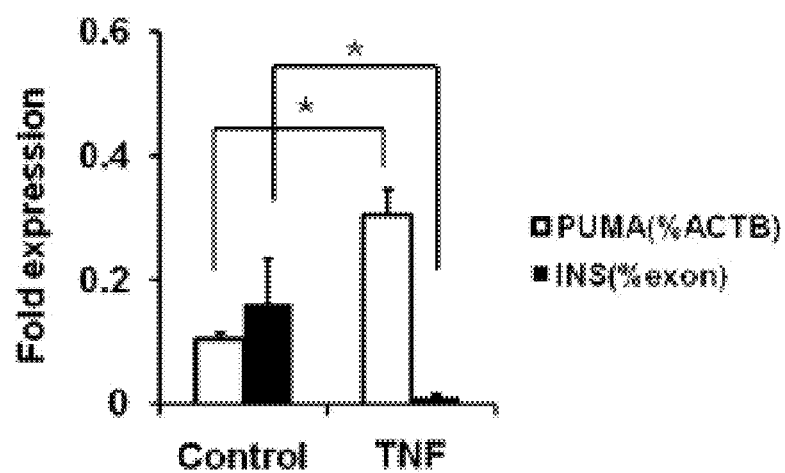
FIG. 12. Increase in PUMA mRNA and decrease in INS precursor mRNA expression in islets stimulated by TNF-α. The expression of PUMA (% ACTB) and INS precursor mRNA (% exon) levels were measured in a set of single human islets, in hextuplicate, cultured for 16 hours in either (FIG. 12A) low-glucose media or (FIG. 12B) high-glucose media with or without 50 ng/ml TNF-α by RT-PCR (*p<0.05, n=3). All data are presented as a mean±SEM.
Figure 12:
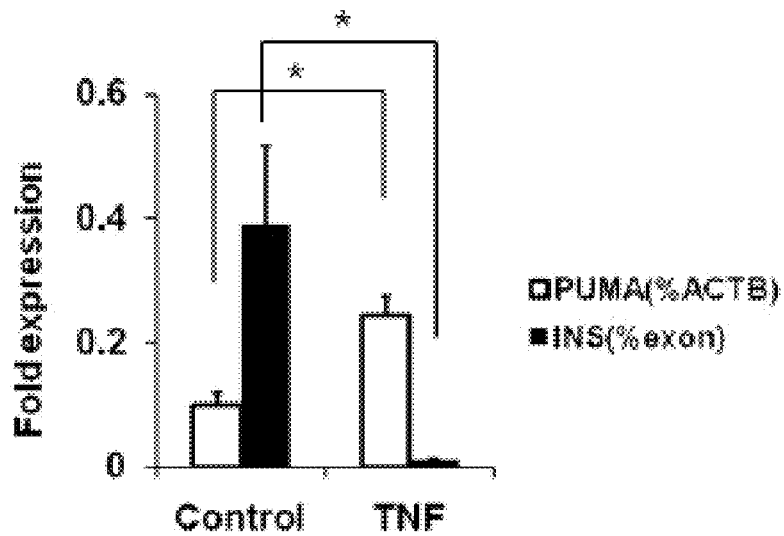

TNF-α Inhibits Preproinsulin Precursor mRNA Synthesis in Human Islets:

The effect of TNF-α and/or IFN-γon β cell function was examined by analyzing the ability of human islets to synthesize and release insulin. The addition of 50 ng/mL TNF-α to either low or high glucose medium did not change insulin release levels during the 16-hour culture period (FIG. 3A). However, glucose-induced, newly synthesized preproinsulin precursor mRNA measured by pre-spliced preproinsulin normalized by pre- and post-spliced preproinsulin was totally abolished by adding TNF-α during incubation (FIG. 3B). The dose dependent effect of TNF-α and/or IFN-γ on preproinsulin precursor mRNA synthesis was also examined. TNF-α as low as 5 ng/mL abrogated the preproinsulin precursor mRNA synthesis response to high glucose culture observed in normal human islets. However, IFNγ alone did not impair glucose induced preproinsulin precursor mRNA synthesis (FIG. 3C). FIG. 12 shows the up-regulation of PUMA mRNA and down-regulation of INS pre-mRNA in human islets by TNF-α (50 ng/ml). PUMA mRNA levels inversely correlated with preproinsulin precursor mRNA levels in islets cultured in high-glucose medium with different dose of TNF-α or TNF-α+IFN-γ treatment (FIG. 3D).

Figure 6A:
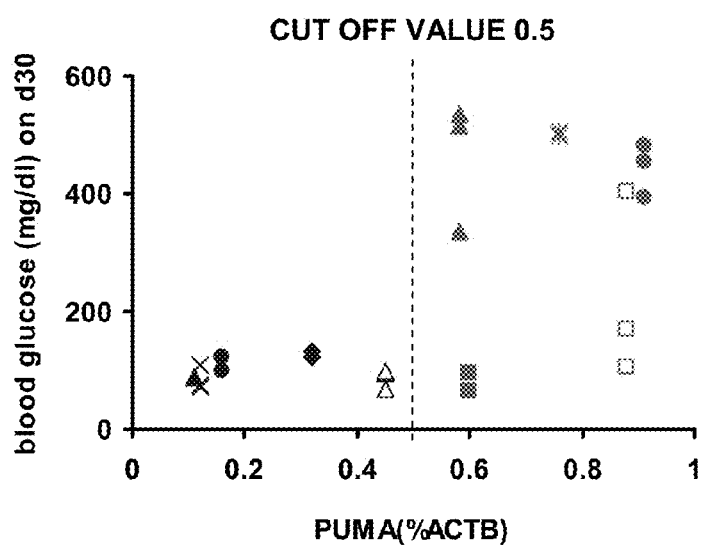
FIG. 6. Cut off PUMA value and changes in blood glucose levels following islet transplantation in diabetic NODscid mice are shown. A) The cut off value of PUMA (% ACTB) for high and low quality islets was set at 0.5 based on the ability of islets to normalize blood glucose. Using this cut off value, all the mice were separated into two groups: reversal or non-reversal of diabetes. B) Changes of blood glucose levels after transplantation of islets below or above the cut off point are shown. The mice which received islets with higher PUMA expression (% ACTB) ≥0.5 did not reverse diabetes, whereas the mice which received islets with lower PUMA expression (% ACTB) <0.5, reversed diabetes after transplantation. The graph indicates that the PUMA mRNA expression levels prior to transplantation indicate islet function after transplantation with the lower PUMA mRNA levels correlating to lower blood glucose levels. Figures C and D) 250 hand-picked siRNA transfected rat islets were transplanted into the liver via the portal vein of diabetic NODscid mice. Changes in blood glucose levels in recipients that received rat islets transfected with (C) PUMA siRNA (3 mice with 3 islet lots) or (D) control siRNA (4 mice with 4 islet lots) one day prior to transplantation.
Figure 6B:
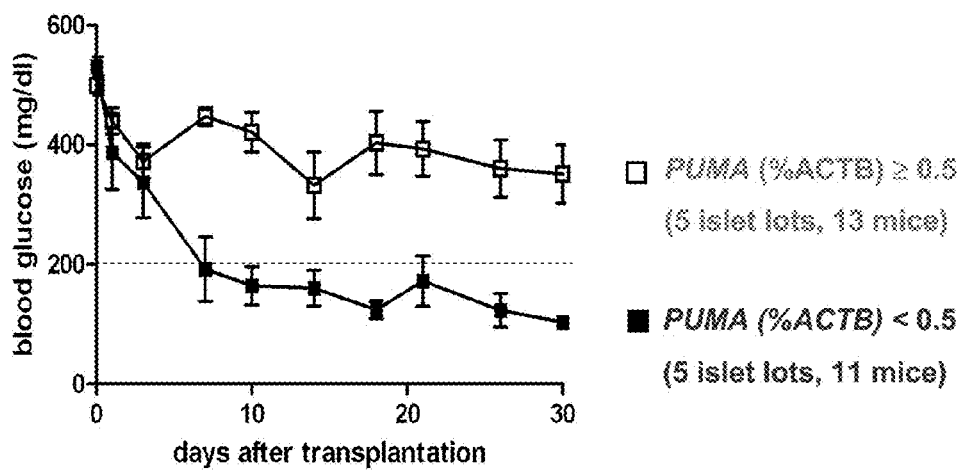
Figure 6C:
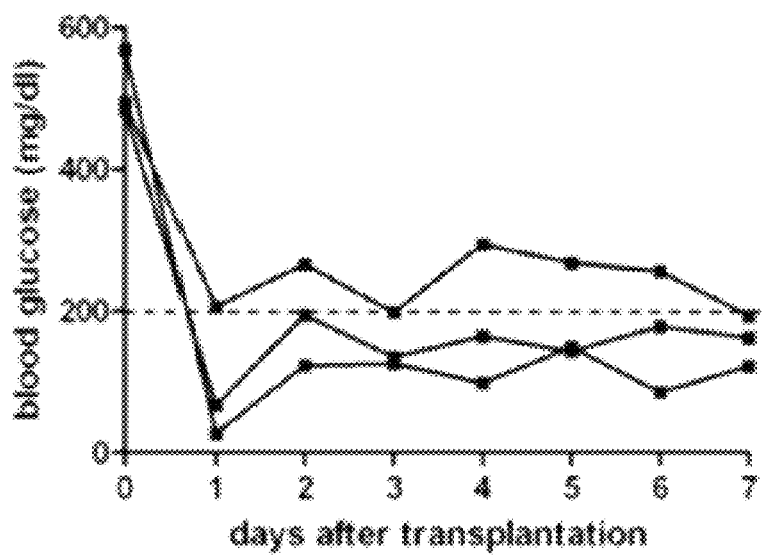
Figure 6D:
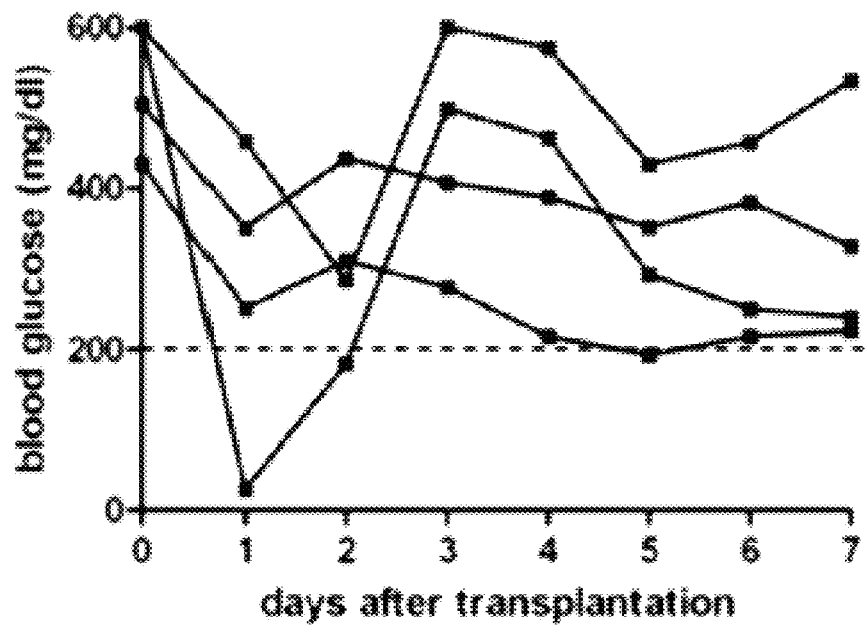
Figure 7:
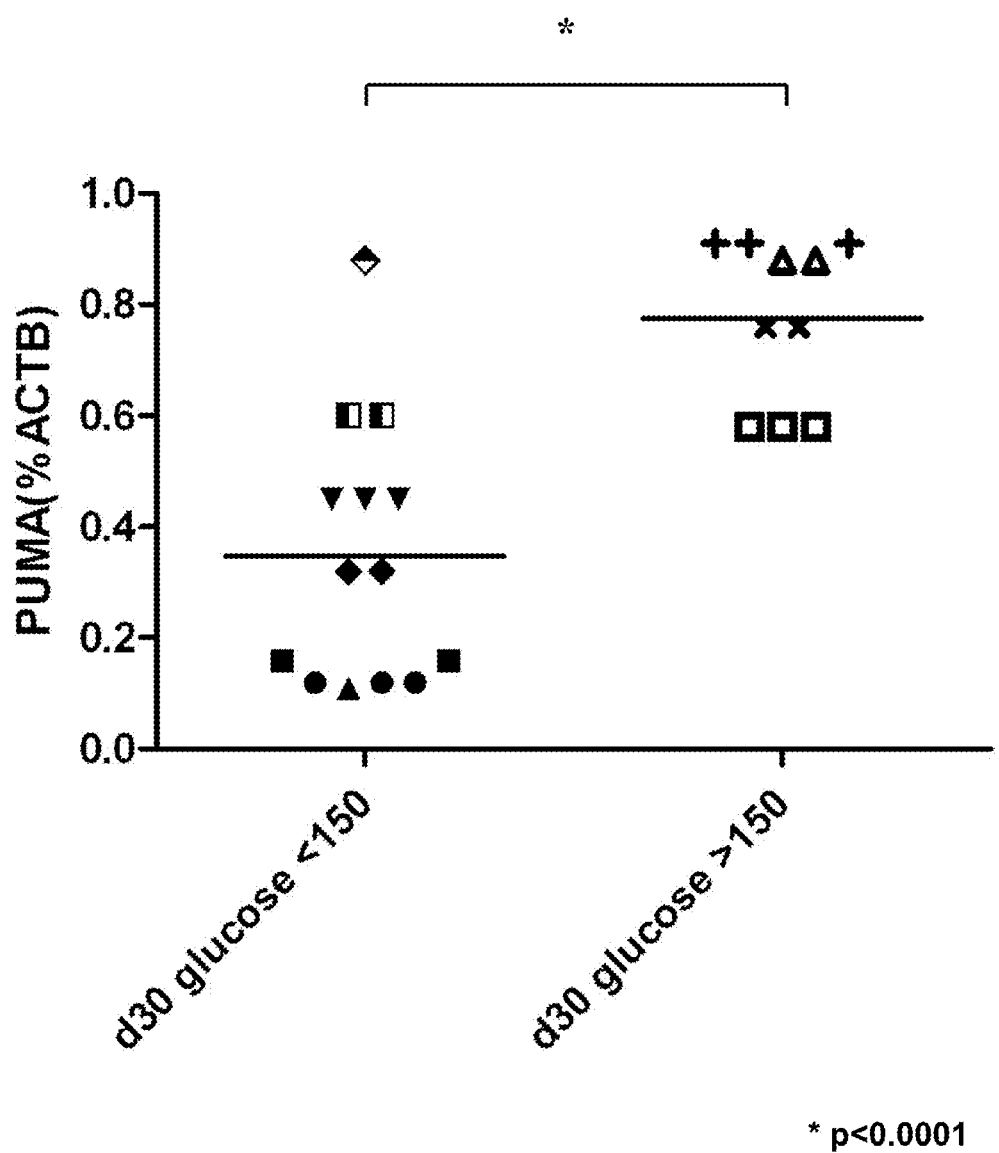
FIG. 7. Comparison of islet PUMA levels between mice that reversed or not reversed diabetes by day 30. The average PUMA expression level of the mice with blood glucose less than 150 mg/dl was significantly lower than that of the mice with blood glucose level higher than 150 mg/dl 30 days after islet transplantation (p<0.0001). The mice received different islet lots. Each lot is shown using a different symbol (+, open squares, solid squares, etc.). One to three mice were transplanted from each islet lot.
Figure 13:
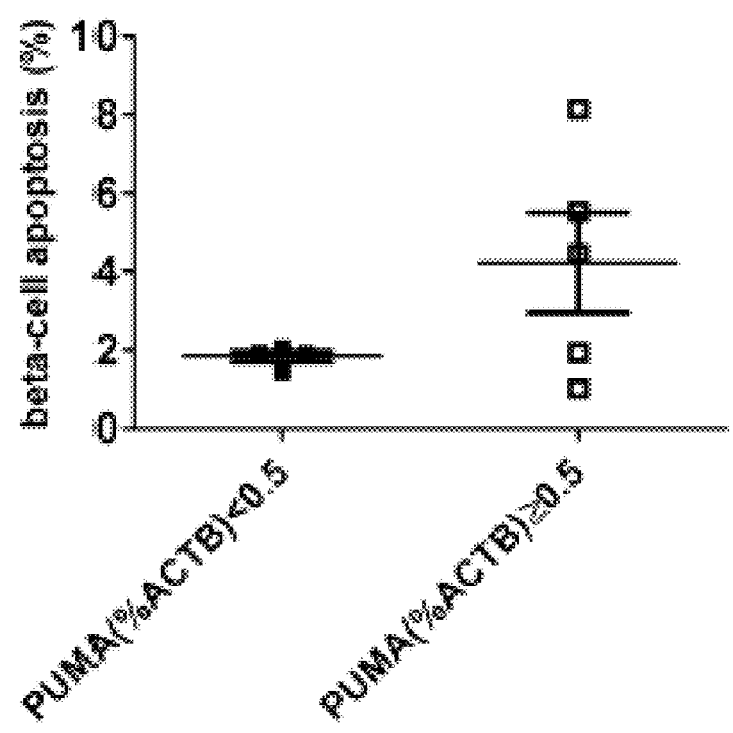
FIG. 13. Basal PUMA expression level and beta-cell apoptosis. Beta-cell apoptosis (%) in human islet lots was examined by TUNEL and insulin staining followed by Laser Scanning Cytometry analysis. Beta—cell apoptosis was consistently low (1.8±0.1%) in the islet lots expressing low basal PUMA (≤0.5 (%ACTB) as shown by the solid squares, n=4; results are not available for one islet lot, while some of the islet lots that expressed higher basal PUMA (≥0.5, shown by the open squares) contained higher levels of beta-cell apoptosis (4.2±1.3%, n=5, P=0.15). Data are presented by mean±SEM.
Figure 14A:
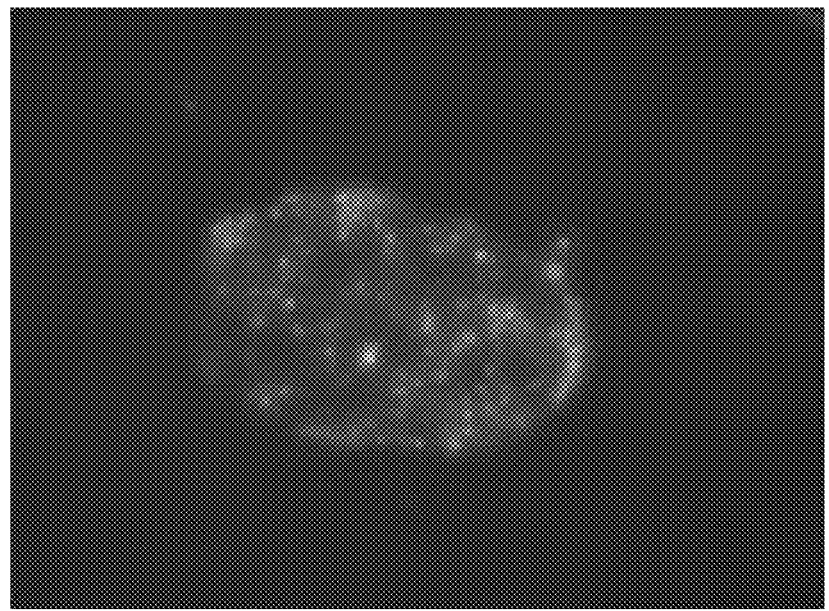
FIG. 14. The efficiency of siRNA transfection of rat islets. Using the transfection reagents, freshly isolated rat islets were transfected overnight with rat PUMA siRNA or control siRNA at a 50 nmol/l concentration in Ham's F-12 medium (Irvine Scientific, Santa Ana, Calif.) containing 5% FBS, 15 mmol/l HEPES, 10 mmol/l nicotinamide prior to transplantation. A) A merged image of a transfected islet: Transfection indicator (SIGLO®) localized in the cells shows green fluorescence (light grey spots). Images were taken at the multiple layers and merged (40×). B) Expression of PUMA mRNA is compared between PUMA siRNA transfected and Control siRNA transfected islets by RT-PCR. Data are presented as a mean±SEM (n=4). C) The transfection efficiency was assessed by dispersing islets into single cells using TRYPLE™ (Invitrogen, Carlsbad, Calif.), stained with DAPI and 6-FAM™ and analyzed by FACS (n=3). D) Representative histogram of transfection indicator positive cells.
Figure 14B:
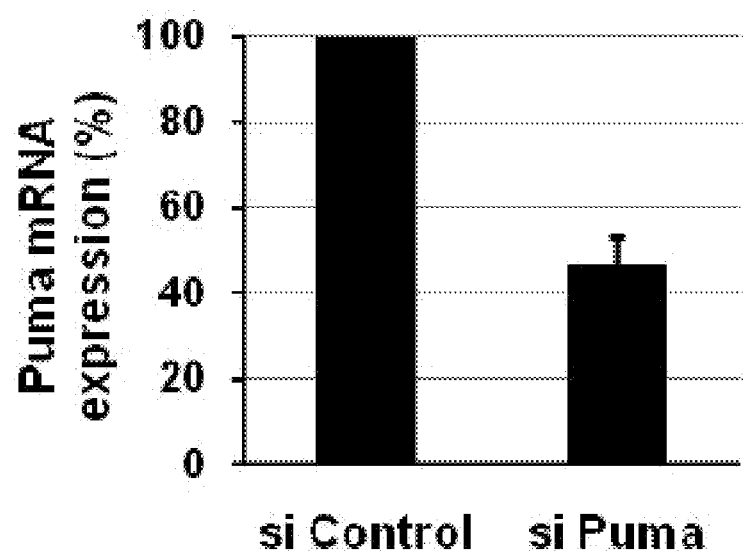
Figure 14C:
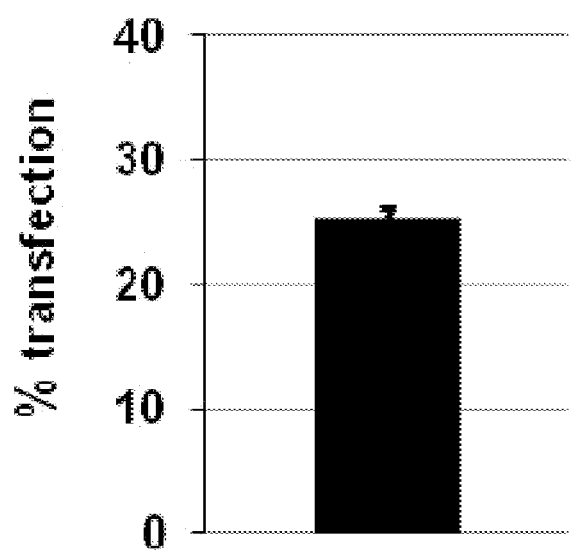
Figure 14D:
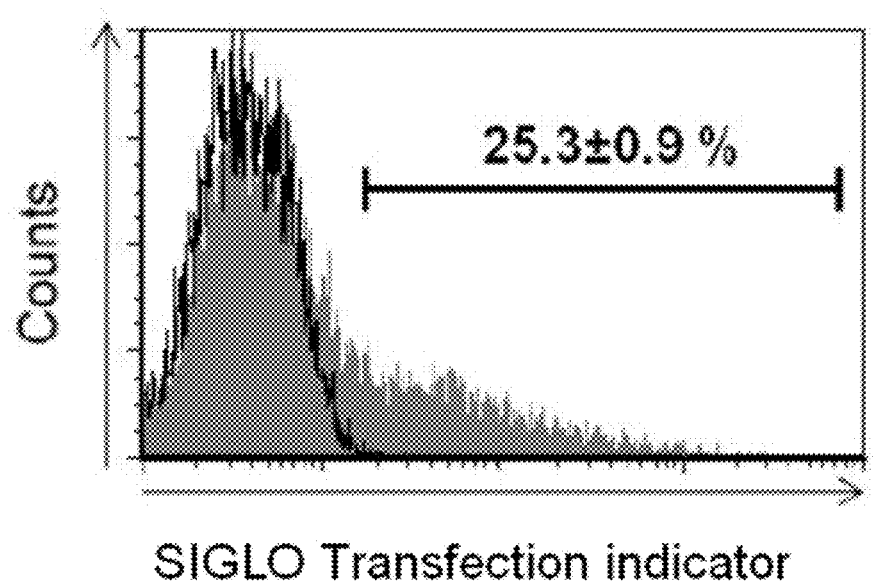

PUMA Expression Level in the Islet Reflects the In Vivo Function to Reverse Hyperglycemia:

To examine whether the PUMA expression in isolated human islets correlates with islet function in vivo, human islets were transplanted into STZ induced diabetic NODscid mice using the standard procedure for in vivo islet quality assessment. Blood glucose levels were measured 30 days after transplantation of 1200 IEQ into the space beneath the renal capsule of diabetic NODscid mice. The level of PUMA mRNA in human islets shortly after isolation was variable between islet lots (FIG. 6A). These variations may be due to exposure to cytokines, including TNF-α, released during cold ischemia and re-warming of the pancreas, islet isolation, and culture [50, 54]. Islet lots that had lower levels of PUMA expression reversed diabetes, while those that had higher PUMA expression failed to reverse diabetes. PUMA expression positively correlated significantly with blood glucose levels 30 days after transplantation (r=0.64, p<0.001) (FIG. 6A). Islet lots that reversed diabetes had a significantly lower PUMA expression (FIG. 13) and achieved euglycemia by day 30, while those that exhibited higher PUMA mRNA tended to contain more apoptotic beta cells and failed to reverse hyperglycemia. Blood glucose levels of mice transplanted with islets expressing lower PUMA mRNA were consistently lower than those receiving islets with higher PUMA mRNA (FIG. 6B). We further tested the role of PUMA on in vivo islet function by transplanting a marginal number of rat islets in which PUMA was suppressed by PUMA siRNA transfection into the liver of diabetic NODscid mice. Although the transfection rate was low (25.3±0.9%) (FIG. 14), PUMA siRNA transfection reduced early islet loss as indicated by blood glucose levels of 153±25 mg/dl in siPUMA group vs. 446±63 mg/dl in siControl group on day 3 (p<0.05). Furthermore, diabetes was reversed in all mice receiving PUMA siRNA-transfected islets, while mice receiving control islets remained diabetic (FIG. 6C and FIG. 6D). These in vivo results indicate that PUMA expression in isolated human islets correlates with islet function following transplantation into diabetic recipients and may be used as an indicator of islet quality.

PUMA mRNA can be used as a molecular biomarker for screening compounds that protect islet from TNF-α induced damage. PUMA mRNA was induced in human islets within 4 hours following TNF-α stimulation in a dose dependent manner. IL-8 and TNF expression accompany the up regulation of PUMA by TNF-α. Therefore, PUMA mRNA, along with IL-8 and TNF, may be used a marker to screen the effect of compounds on islets. To test such possibilities, randomly selected compounds were screened using our single islet assay system to test either increase or decrease of PUMA expression induced by 5 ng/mL TNF-α. Pre-incubation with Etanercept, a recombinant protein of human soluble TNFR2 coupled to Fc portion of human IgG that binds to TNF-α and inhibits its attachment to endogenous TNF cell surface receptors, prevented TNF-α induced up regulation of PUMA (FIG. 4A), IL-8 (FIG. 4B) and TNF (FIG. 4C) expression. The result indicates complete neutralization of the added and secreted TNF-α in our in vitro assay system. Pre-incubation of islets with a tyrosine kinase inhibitor, Imatinib, and Janus Kinase (JAK) inhibitor prior to TNF-α stimulation also reduced the up regulation of PUMA, IL-8 and TNF expression as compared to the control (vehicle alone), whereas the immunosuppressive drugs (Cyclosporine, FK506, and Rapamicin) showed no suppression. Accordingly, an additional embodiment provides a method protecting an islet cell from apoptosis comprising administering a JAK inhibitor (such as Imatinib), and optionally, a tyrosine kinase inhibitor to the islet cell.

Figure 15:
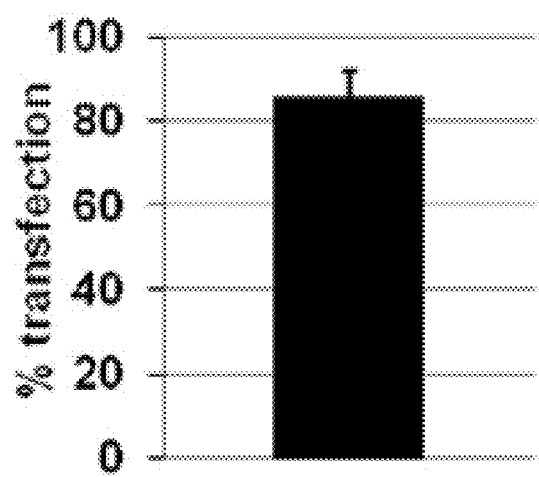
FIG. 15. The efficiency of siRNA transfection of INS-1 cells. A) The transfection efficiency was assessed by transfecting INS-1 cells with the SIGLO® transfection indicator labeled with 6-FAM and analyzed by FACS (n=3). B) Expression of PUMA mRNA is compared between PUMA siRNA transfected and Control siRNA transfected INS-1 cells by RT-PCR (n=3). All data are presented as a mean±SEM.
Figure 15:
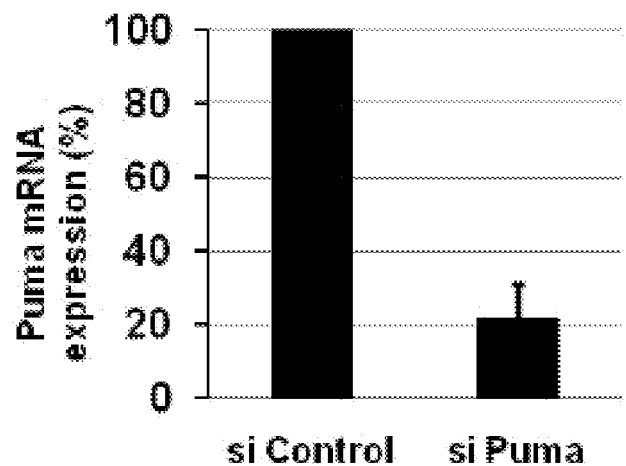
Figure 16:
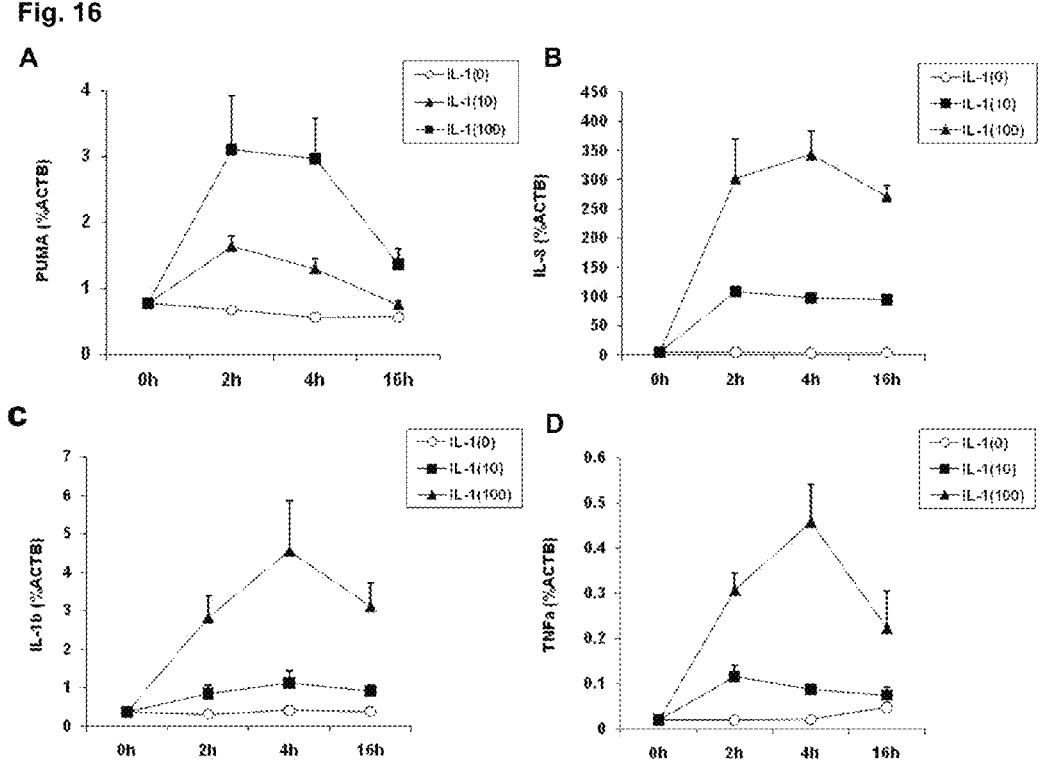
FIG. 16. IL-1β up-regulates PUMA mRNA in human islets. Single islets in sextuplicate were stimulated with or without recombinant IL-1β (0.10 and 100 U/mL) for up to 16 hours. A) PUMA, B) IL-8, C) endogenous IL-1B and D) endogenous TNF mRNA in islets were normalized by β actin (% ACTB) mRNA assessed by RT-PCR (n=1). IL-1β induced PUMA, IL-8, endogenous IL-1 and TNF in human islets.

Measuring mRNA expression of tumor necrosis factor receptor super family (TNFRSF) 1A and 1B on human islets and acinar cell clusters revealed that human islet expresses abundant TNFRSF1A (TNFR1). RT-PCR was performed in triplicate samples of either 10 islets or 10 acinar cell clusters prepared from two different pancreases and the results are shown in FIG. 1. Transfection efficiency of siRNA transfecting INS-1 cells is shown in FIG. 15A. Expression of PUMA mRNA is compared between PUMA siRNA transfected and Control siRNA transfected INS-1 cells by RT-PCR (n=3) in FIG. 15B.

In summary, the present discovery demonstrates for the first time TNF-α induced PUMA expression in human islets via the activation of NFκB, which leads β cells to apoptosis through an intrinsic pathway. PUMA mRNA expression mediated by TNF-stimulation can be used as a biomarker to evaluate various compounds/drugs to assess their effect on β cell function and survival. Tyrosine kinase inhibitor or JAK inhibitors may be used alone or in conjunction with other anti-PUMA technology, such as PUMA siRNA to protect islets. Furthermore the assay system using single human islet would facilitate the development of a high-throughput system for the discovery of new drugs that protect islet cell death, leading to discovery of new drugs for prevention and treatment of T1DM as well as T2DM. The significance of PUMA as a biomarker and manipulation of PUMA levels as an indicator islet health and a therapy is described.

Certain embodiments of the invention are described in detail, using specific examples, sequences, and drawings. The enumerated embodiments are not intended to limit the invention to those embodiments, as the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. Unless defined otherwise, all technical and scientific terms used herein have the same meaning as commonly understood by one of ordinary skill in the art to which this invention belongs. All publications and/or patents are incorporated by reference as though fully set forth herein.

REFERENCES

1. Eizirik, D. L., and Mandrup-Poulsen, T. 2001. A choice of death—the signal-transduction of immune-mediated beta-cell apoptosis. Diabetologia 44:2115-2133.
2. Stephens, L. A., Thomas, H. E., Ming, L., Grell, M., Darwiche, R., Volodin, L., and Kay, T. W. 1999. Tumor necrosis factor-alpha-activated cell death pathways in NIT-1 insulinoma cells and primary pancreatic beta cells. Endocrinology 140:3219-3227.
3. Jacob, C. O., Aiso, S., Michie, S. A., McDevitt, H. O., and Acha-Orbea, H. 1990. Prevention of diabetes in nonobese diabetic mice by tumor necrosis factor (TNF): similarities between TNF-alpha and interleukin 1. Proc Natl Acad Sci USA 87:968-972.
4. Satoh, J., Seino, H., Abo, T., Tanaka, S., Shintani, S., Ohta, S., Tamura, K., Sawai, T., Nobunaga, T., Oteki, T., et al. 1989. Recombinant human tumor necrosis factor alpha suppresses autoimmune diabetes in nonobese diabetic mice. J Clin Invest 84:1345-1348.
5. Yang, X. D., Tisch, R., Singer, S. M., Cao, Z. A., Liblau, R. S., Schreiber, R. D., and McDevitt, H. O. 1994. Effect of tumor necrosis factor alpha on insulin-dependent diabetes mellitus in NOD mice. I. The early development of autoimmunity and the diabetogenic process. J Exp Med 180:995-1004.
6. Held, W., MacDonald, H. R., Weissman, I. L., Hess, M. W., and Mueller, C. 1990. Genes encoding tumor necrosis factor alpha and granzyme A are expressed during development of autoimmune diabetes. Proc Natl Acad Sci USA 87:2239-2243.
7. Mueller, C., Held, W., Imboden, M. A., and Carnaud, C. 1995. Accelerated beta-cell destruction in adoptively transferred autoimmune diabetes correlates with an increased expression of the genes coding for TNF-alpha and granzyme A in the intra-islet infiltrates. Diabetes 44:112-117.
8. Picarella, D. E., Kratz, A., Li, C. B., Ruddle, N. H., and Flavell, R. A. 1993. Transgenic tumor necrosis factor (TNF)-alpha production in pancreatic islets leads to insulitis, not diabetes. Distinct patterns of inflammation in TNF-alpha and TNF-beta transgenic mice. J Immunol 150:4136-4150.
9. Suk, K., Kim, S., Kim, Y. H., Kim, K. A., Chang, I., Yagita, H., Shong, M., and Lee, M. S. 2001. IFN-gamma/TNF-alpha synergism as the final effector in autoimmune diabetes: a key role for STAT1/IFN regulatory factor-1 pathway in pancreatic beta cell death. J Immunol 166:4481-4489.
10. Hotamisligil, G. S., Murray, D. L., Choy, L. N., and Spiegelman, B. M. 1994. Tumor necrosis factor alpha inhibits signaling from the insulin receptor. Proc Natl Acad Sci USA 91:4854-4858.
11. Uysal, K. T., Wiesbrock, S. M., Marino, M. W., and Hotamisligil, G. S. 1997. Protection from obesity-induced insulin resistance in mice lacking TNF-alpha function. Nature 389:610-614.
12. Steinberg, G. R., Michell, B. J., van Denderen, B. J., Watt, M. J., Carey, A. L., Fam, B. C., Andrikopoulos, S., Proietto, J., Gorgun, C. Z., Carling, D., et al. 2006. Tumor necrosis factor alpha-induced skeletal muscle insulin resistance involves suppression of AMP-kinase signaling. Cell Metab 4:465-474.
13. Tesz, G. J., Guilherme, A., Guntur, K. V., Hubbard, A. C., Tang, X., Chawla, A., and Czech, M. P. 2007. Tumor necrosis factor alpha (TNFalpha) stimulates Map4k4 expression through TNFalpha receptor 1 signaling to c-Jun and activating transcription factor 2. J Biol Chem 282:19302-19312.
14. Bouzakri, K., and Zierath, J. R. 2007. MAP4K4 gene silencing in human skeletal muscle prevents tumor necrosis factor-alpha-induced insulin resistance. J Biol Chem 282:7783-7789.
15. Plomgaard, P., Bouzakri, K., Krogh-Madsen, R., Mittendorfer, B., Zierath, J. R., and Pedersen, B. K. 2005. Tumor necrosis factor-alpha induces skeletal muscle insulin resistance in healthy human subjects via inhibition of Akt substrate 160 phosphorylation. Diabetes 54:2939-2945.
16. Karin, M., and Lin, A. 2002. NF-kappaB at the crossroads of life and death. Nat Immunol 3:221-227.
17. Aggarwal, B. B. 2003. Signalling pathways of the TNF superfamily: a double-edged sword. Nat Rev Immunol 3:745-756.
18. Wajant, H., Pfizenmaier, K., and Scheurich, P. 2003. Tumor necrosis factor signaling. Cell Death Differ 10:45-65.
19. Hengartner, M. O. 2000. The biochemistry of apoptosis. Nature 407:770-776.
20. Danial, N. N., and Korsmeyer, S. J. 2004. Cell death: critical control points. Cell 116:205-219.
21. McKenzie, M. D., Carrington, E. M., Kaufmann, T., Strasser, A., Huang, D. C., Kay, T. W., Allison, J., and Thomas, H. E. 2008. Proapoptotic BH3-only protein Bid is essential for death receptor-induced apoptosis of pancreatic beta-cells. Diabetes 57:1284-1292.
22. Grunnet, L. G., Aikin, R., Tonnesen, M. F., Paraskevas, S., Blaabjerg, L., Storling, J., Rosenberg, L., Billestrup, N., Maysinger, D., and Mandrup-Poulsen, T. 2009. Proinflammatory cytokines activate the intrinsic apoptotic pathway in beta-cells. Diabetes 58:1807-1815.
23. Sun, Q., Ming, L., Thomas, S. M., Wang, Y., Chen, Z. G., Ferris, R. L., Grandis, J. R., Zhang, L., and Yu, J. 2009. PUMA mediates EGFR tyrosine kinase inhibitor-induced apoptosis in head and neck cancer cells. Oncogene 28:2348-2357.
24. Vousden, K. H. 2005. Apoptosis. p53 and PUMA: a deadly duo. Science 309:1685-1686.
25. Nakano, K., and Vousden, K. H. 2001. PUMA, a novel proapoptotic gene, is induced by p53. Mol Cell 7:683-694.
26. Yu, J., Wang, Z., Kinzler, K. W., Vogelstein, B., and Zhang, L. 2003. PUMA mediates the apoptotic response to p53 in colorectal cancer cells. Proc Natl Acad Sci USA 100:1931-1936.
27. You, H., Pellegrini, M., Tsuchihara, K., Yamamoto, K., Hacker, G., Erlacher, M., Villunger, A., and Mak, T. W. 2006. FOXO3a-dependent regulation of PUMA in response to cytokine/growth factor withdrawal. J Exp Med 203:1657-1663.
28. Reimertz, C., Kogel, D., Rami, A., Chittenden, T., and Prehn, J. H. 2003. Gene expression during ER stress-induced apoptosis in neurons: induction of the BH3-only protein Bbc3/PUMA and activation of the mitochondrial apoptosis pathway. J Cell Biol 162:587-597.
29. Wu, B., Qiu, W., Wang, P., Yu, H., Cheng, T., Zambetti, G. P., Zhang, L., and Yu, J. 2007. p53 independent induction of PUMA mediates intestinal apoptosis in response to ischaemia-reperfusion. Gut 56:645-654.
30. Toth, A., Jeffers, J. R., Nickson, P., Min, J. Y., Morgan, J. P., Zambetti, G. P., and Erhardt, P. 2006. Targeted deletion of PUMA attenuates cardiomyocyte death and improves cardiac function during ischemia-reperfusion. Am J Physiol Heart Circ Physiol 291: H52-60.
31. Wang, P., Qiu, W., Dudgeon, C., Liu, H., Huang, C., Zambetti, G. P., Yu, J., and Zhang, L. 2009. PUMA is directly activated by NF-kappaB and contributes to TNF-alpha-induced apoptosis. Cell Death Differ 16:1192-1202.
32. Omori K, M. M., Todorov I, Rawson J, Shiang K. D, Kandeel F, Mullen Y. 2010. Microassay for glucose-induced preproinsulin mRNA expression to assess islet functional potency for islet transplantation. Transplantation.
33. Ortis, F., Pirot, P., Naamane, N., Kreins, A. Y., Rasschaert, J., Moore, F., Theatre, E., Verhaeghe, C., Magnusson, N. E., Chariot, A., et al. 2008. Induction of nuclear factor-kappaB and its downstream genes by TNF-alpha and IL-1 beta has a pro-apoptotic role in pancreatic beta cells. Diabetologia 51:1213-1225.
34. Eizirik, D. L., Colli, M. L., and Ortis, F. 2009. The role of inflammation in insulitis and beta-cell loss in type 1 diabetes. Nat Rev Endocrinol 5:219-226.
35. Mitsuhashi, M., Ogura, M., Endo, K., Obara, K., Izutsu, H., Targan, S. R., Maemura, M., Tachikawa, D., and Shinagawa, A. 2008. Ex vivo induction of mRNA in 36. Mitsuhashi, M., and Targan, S. R. 2008. Ex vivo simulation of IgG Fc and T-cell receptor functions: an application to inflammatory bowel disease. Inflamm Bowel Dis 14:1061-1067.
37. Thomas, H. E., Darwiche, R., Corbett, J. A., and Kay, T. W. 1999. Evidence that beta cell death in the nonobese diabetic mouse is Fas independent. J Immunol 163:1562-1569.
38. Hughes, K. J., Chambers, K. T., Meares, G. P., and Corbett, J. A. 2009. Nitric oxides mediates a shift from early necrosis to late apoptosis in cytokine-treated {beta}-cells that is associated with irreversible DNA damage. Am J Physiol Endocrinol Metab.
39. Kwon, G., Xu, G., Marshall, C. A., and McDaniel, M. L. 1999. Tumor necrosis factor alpha-induced pancreatic beta-cell insulin resistance is mediated by nitric oxide and prevented by 15-deoxy-Delta12,14-prostaglandin J2 and aminoguanidine. A role for peroxisome proliferator-activated receptor gamma activation and inos expression. J Biol Chem 274:18702-18708.
40. Kim, H. E., Choi, S. E., Lee, S. J., Lee, J. H., Lee, Y. J., Kang, S. S., Chun, J., and Kang, Y. 2008. Tumour necrosis factor-alpha-induced glucose-stimulated insulin secretion inhibition in INS-1 cells is ascribed to a reduction of the glucose-stimulated Ca+ influx. J Endocrinol 198:549-560.
41. Mastrandrea, L., Yu, J., Behrens, T., Buchlis, J., Albini, C., Fourtner, S., and Quattrin, T. 2009. Etanercept treatment in children with new-onset type 1 diabetes: pilot randomized, placebo-controlled, double-blind study. Diabetes Care 32:1244-1249.
42. Louvet, C., Szot, G. L., Lang, J., Lee, M. R., Martinier, N., Bollag, G., Zhu, S., Weiss, A., and Bluestone, J. A. 2008. Tyrosine kinase inhibitors reverse type 1 diabetes in nonobese diabetic mice. Proc Natl Acad Sci USA 105:18895-18900.
43. Lv, N., Kim, E. K., Song, M. Y., Choi, H. N., Moon, W. S., Park, S. J., Park, J. W., Kwon, K. B., and Park, B. H. 2009. JANEX-1, a JAK3 inhibitor, protects pancreatic islets from cytokine toxicity through downregulation of NF-kappaB activation and the JAK/STAT pathway. Exp Cell Res 315:2064-2071.
44. Mitsuhashi, M., Tomozawa, S., Endo, K., and Shinagawa, A. 2006. Quantification of mRNA in whole blood by assessing recovery of RNA and efficiency of cDNA synthesis. Clin Chem 52:634-642.
45. Mitsuhashi, M., Keller, C., and Akitaya, T. 1992. Gene manipulation on plastic plates. Nature 357:519-520.
46. Morrison, T. B., Weis, J. J., and Wittwer, C. T. 1998. Quantification of low-copy transcripts by continuous SYBR Green I monitoring during amplification. Biotechniques 24:954-958, 960, 962.
47. Mitsuhashi, M., Endo, K., Obara, K., Izutsu, H., Ishida, T., Chikatsu, N., and Shinagawa, A. 2008. Ex vivo simulation of the action of antileukemia drugs by measuring apoptosis-related mRNA in blood. Clin Chem 54:673-681.
48. Mitsuhashi M, E. K., Obara K, Izutsu H, Ishida T, Chikatsu N, Shinagawa A. 2008. Quantification of Drug-Induced mRNA in Human Whole Blood ex vivo. Clinical Medicine: Blood Disorders 1:1-11.
49. Omori, K., Valiente, L., Orr, C., Rawson, J., Ferreri, K., Todorov, I., Al-Abdullah, I. H., Medicherla, S., Potter, A. A., Schreiner, G. F., et al. 2007. Improvement of human islet cryopreservation by a p38 MAPK inhibitor. Am J Transplant 7:1224-1232.
50. Ito, T., Omori, K., Rawson, J., Todorov, I., Asari, S., Kuroda, A., Shintaku, J., Itakura, S., Ferreri, K., Kandeel, F., et al. 2008. Improvement of canine islet yield by donor pancreas infusion with a p38MAPK inhibitor. Transplantation 86:321-329.
51. Gurzov E N, Germano C M, Cunha D A, et al. (2010) PUMA activation contributes to pancreatic beta cell apoptosis induced by pro-inflammatory cytokines and endoplasmic reticulum stress. J Biol. Chem.
52. Todorov I, Nair I, Avakian-Mansoorian A, et al. (2010) Quantitative assessment of beta-cell apoptosis and cell composition of isolated, undisrupted human islets by laser scanning cytometry. Transplantation 90: 836-842.
53. Itakura S, Asari S, Rawson J, et al. (2007) Mesenchymal stem cells facilitate the induction of mixed hematopoietic chimerism and islet allograft tolerance without GVHD in the rat. Am J Transplant 7: 336-346.
54. Hanley S, Liu S, Lipsett M, et al. (2006) Tumor necrosis factor-alpha production by human islets leads to postisolation cell death. Transplantation 82: 813-818.
55. Hagerkvist R, Sandler S, Mokhtari D, Welsh N (2007) Amelioration of diabetes by imatinib mesylate (Gleevec): role of beta-cell NF-kappaB activation and anti-apoptotic preconditioning. FASEB J 21: 618-628.
56. Matsuda T, Omori K, Vuong T, et al. (2005) Inhibition of p38 pathway suppresses human islet production of pro-inflammatory cytokines and improves islet graft function. Am J Transplant 5: 484-493.
57. Omori K, Todorov I, Shintaku J, et al. (2010) P38alpha-selective mitogen-activated protein kinase inhibitor for improvement of cultured human islet recovery. Pancreas 39: 436-443.
58. De Vos K, Goossens V, Boone E, et al. (1998) The 55-kDa tumor necrosis factor receptor induces clustering of mitochondria through its membrane-proximal region. The Journal of biological chemistry 273: 9673-9680.
59. Desagher S, Martinou J C (2000) Mitochondria as the central control point of apoptosis. Trends Cell Biol 10: 369-377.
60. Niizuma K, Endo H, Nito C, Myer D J, Chan P H (2009) Potential role of PUMA in delayed death of hippocampal CA1 neurons after transient global cerebral ischemia. Stroke 40: 618-625.

The invention claimed is:

1. A method of treating hyperglycemia or diabetes in a subject comprising:
   determining whether an islet is a candidate for transplant, comprising:
   quantifying an expression level of p53 upregulated modulator of apoptosis (PUMA) messenger RNA (mRNA) comprising:
   reverse transcribing an RNA sample from the islet, forming a first cDNA sample, and
   amplifying the first cDNA sample to determine the expression level of PUMA mRNA, wherein the expression level of PUMA is determined by quantitative reverse transcriptase polymerase chain reaction (qRT-PCR);
   quantifying an expression level of pre-spliced preproinsulin mRNA comprising;
   reverse transcribing the RNA sample from the islet, forming a second cDNA sample, and
   amplifying the second cDNA sample to determine the expression level of pre-spliced preproinsulin mRNA, wherein the expression level of pre-spliced preproinsulin mRNA is determined by qRT-PCR;
   determining the islet is a candidate for transplant when the expression level of pre-spliced preproinsulin mRNA is greater than the expression level of PUMA mRNA; and
   transplanting islets that are equivalent to the islet determined to be a candidate for transplant into the subject to treat the hyperglycemia or diabetes.

2. The method of claim 1, wherein the expression level of PUMA is normalized to an expression level of a control gene and the expression level of pre-spliced preproinsulin mRNA is normalized to an expression level of pre- and post-spliced preproinsulin mRNA.

3. The method of claim 1, wherein the islet is a candidate for transplant when the expression level of PUMA mRNA is less than a cutoff value of 0.5.

4. The method of claim 1, wherein the subject is suffering from hyperglycemia or diabetes and the transplanted islets reverse the hyperglycemia or diabetes.

5. The method of claim 1, wherein one or more nucleotide probe pairs are used to perform qRT-PCR of pre-spliced preproinsulin mRNA.

6. The method of claim 5, wherein the one or more nucleotide probe pairs comprise:
- AGGTGGGCTCAGGATTCCA (SEQ ID NO.1) (In1 upstream) and TCACCCCCACATGCTTCAC (SEQ ID NO.2) (In1 downstream);
- ACTCGCCCCTCAAACAAATG (SEQ ID NO.3) (In2 upstream) and TGAATCTGCGGTCATCAAATG (SEQ ID NO.4) (In2 downstream);
- CTCTGCCTCGCCGCTGTTC (SEQ ID NO.5) (In2Ex3 upstream) and TCCACAATGCCACGCTTCTG (SEQ ID NO.6) (In2Ex3 downstream);
- GCAGCCTTTGTGAACCAACA (SEQ ID NO.7) (Ex2a upstream) and TTCCCCGCACACTAGGTAGAGA (SEQ ID NO.8) (Ex2a downstream);
- GGGAACGAGGCTTCTTCTACAC (SEQ ID NO.9) (Ex2b upstream) and CCACAATGCCACGCTTCTG (SEQ ID NO.10) (Ex2b downstream); and
- CATTGTGGAACAATGCTGTACCA (SEQ ID NO.11) (Ex3 upstream) and GCCTGCGGGCTGCGTCTA (SEQ ID NO.12) (Ex3 downstream).

* * * * *

UNITED STATES PATENT AND TRADEMARK OFFICE
CERTIFICATE OF CORRECTION

PATENT NO. : 9,758,826 B2  
APPLICATION NO. : 13/163326  
DATED : September 12, 2017  
INVENTOR(S) : Yoko Mullen et al.

Page 1 of 1

It is certified that error appears in the above-identified patent and that said Letters Patent is hereby corrected as shown below:

In the Specification

Government Interest section, Column 1, Lines 13-16, please delete:
"The present invention was made with govermnent support under National Institutes of Health grant number U42RR16607. The government may have certain rights in the present invention."

And insert:
--This invention was made with government support under U42 RR016607 awarded by the National Institutes of Health. The government has certain rights in the invention.--

Signed and Sealed this  
Eighth Day of April, 2025

Coke Morgan Stewart  
*Acting Director of the United States Patent and Trademark Office*